(12) United States Patent
Shapiro

(10) Patent No.: US 6,444,221 B1
(45) Date of Patent: *Sep. 3, 2002

(54) METHODS OF TREATING CHRONIC INFLAMMATORY DISEASES USING CARBONYL TRAPPING AGENTS

(76) Inventor: Howard K. Shapiro, 214 Price Ave., Apt. F-32, Narberth, PA (US) 19072

( * ) Notice: Subject to any disclaimer, the term of this patent is extended or adjusted under 35 U.S.C. 154(b) by 0 days.

This patent is subject to a terminal disclaimer.

(21) Appl. No.: 09/416,120

(22) Filed: Oct. 12, 1999

Related U.S. Application Data

(63) Continuation-in-part of application No. 08/473,786, filed on Jun. 7, 1995, now abandoned, which is a continuation-in-part of application No. 07/906,909, filed on Jun. 30, 1992, now abandoned.

(51) Int. Cl.$^7$ .................................................. A61K 9/48

(52) U.S. Cl. ........................ 424/451; 424/457; 424/464; 424/468; 424/439; 424/442; 514/458; 514/55; 514/57

(58) Field of Search ................................ 424/451, 457, 424/464, 468, 439, 442; 514/55, 57, 458

(56) References Cited

U.S. PATENT DOCUMENTS

| | | | | |
|---|---|---|---|---|
| 4,154,823 A | * | 5/1979 | Schutt | 424/195 |
| 5,668,117 A | * | 9/1997 | Shapiro | 514/55 |
| 6,090,414 A | * | 7/2000 | Passwater et al. | 424/702 |

FOREIGN PATENT DOCUMENTS

JP 63-156726 A * 6/1988

* cited by examiner

*Primary Examiner*—Peter F. Kulkosky
*Assistant Examiner*—Liliana Di Nola-Baron

(57) ABSTRACT

These and other objects of this invention are achieved by providing a novel method and compositions for the clinical treatment of chronic inflammatory diseases. This invention involves use of systemically administered compositions which include primary amine derivatives of benzoic acid as carbonyl trapping agents. These primary therapeutic agents act by chemically binding to and sequestering the aldehyde and/or ketone products of lipid peroxidation. Increased levels of lipid peroxidation have been repeatedly demonstrated as a part of the non-enzymatic "inflammatory cascade" process which underlies the secondary etiology of chronic inflammatory diseases. p-Aminobenzoic acid (or PABA) is an example of the primary therapeutic agent of the present invention. PABA has a small molecular weight, is water soluble, has a primary amine group that reacts with carbonyl-containing metabolites under physiological conditions and is tolerated by the body in relatively high dosages and for extended periods. The carbonyl sequestering agents are used in combination with at least one co-agent so as to produce an additional beneficial physiological effect of an anti-inflammatory nature. Such compositions are administered systemically entirely via the oral route. Co-agents of the present invention include anti-oxidants and free radical trapping compounds (e.g., α-tocopherol), compounds having indirect anti-oxidant activity (e.g., selenium), vitamins (e.g., pyridoxine HCl), compounds which facilitate kidney drug elimination (e.g., glycine), metabolites at risk of depletion (e.g., pantothenic acid), sulfhydryl containing chemicals (e.g., methionine), compounds which facilitate glutathione activity (e.g., N-acetylcysteine), and non-absorbable polyamine co-agents (e.g., chitosan).

26 Claims, No Drawings

METHODS OF TREATING CHRONIC INFLAMMATORY DISEASES USING CARBONYL TRAPPING AGENTS

RELATED APPLICATIONS

This patent application is a continuation-in-part of the U.S. patent application Ser. No. 08/473,786 filed Jun. 7, 1995 for METHODS OF TREATING CHRONIC INFLAMMATORY DISEASES USING CARBONYL TRAPPING AGENTS, now abandoned, which in turn was a continuation-in-part of U.S. patent application Ser. No. 07/906,909 filed Jun. 30, 1992 for METHODS OR TREATING CHRONIC INFLAMMATORY DISEASES AND ETIOLOGICALLY RELATED SYMPTOMOLOGY USING CARBONYL TRAPPING AGENTS IN COMBINATION WITH ANTI-OXIDANTS AND RELATED AGENTS, now abandoned.

BACKGROUND OF THE INVENTION

1. Field of the Invention

This invention relates to the clinical treatment of chronic inflammatory disorders. For purposes of this invention, the category of chronic inflammatory disorders includes chronic gingivitis, chronic periodontitis, chronic autoimmune gastritis, ileitis, colitis, interstitial cystitis, arthritis, tendinitis, cumulative trauma disorders, systemic lupus erythematosus, autoimmune vasculitis, asbestosis, silicosis, Lyme disease, inflammatory myopathies, Duchenne muscular dystrophy, epilepsy, inflammatory neuropathies, myasthenia gravis, multiple sclerosis, inflammatory site edema, post-event acute central nervous system trauma, stroke, and myocardial infarction.

2. Description of Prior Art

Numerous prior art publications disclose that vitamin E functions physiologically as a lipid-soluble anti-oxidant free radical trapping agent. Prior art publications describe methionine as a water-soluble agent, an essential amino acid, an anti-oxidant and a free radical trapping agent.

p-Aminobenzoic acid (PABA) is known as a water-soluble B vitamin, and several published studies have presented evidence to the effect that PABA functions, in part, as a weak anti-oxidant and a weak free radical trapping agent (Maksimov, O B and Rebachuk, N M, 1985, Table 2; Pryor, WA et al., 1976, pg. 201).

Insofar as benzoic acid or derivatives thereof have been recognized as anti-oxidants or free radical trapping agents, their mechanism of action is understood to consist of hydroxyl radical trapping by the benzene ring (Grootveld, M and Halliwell, B, 1988; Halliwell, B and Gutteridge, J M, 1985, pp. 105 and 130; Richmond, R et al., 1981; Repine, J E et al., 1979, pg. 1642). This has been explicitly demonstrated for PABA (Nakken, K F, 1964, pp. 446, 448, 454–457; Nakken, K F and Pihl, A, 1966, pp. 21, 22, 24, 25 and 28). Likewise, mannitol is recognized as an anti-oxidant based on its ability to scavenge hydroxyl radicals (Halliwell, B and Gutteridge, J M, 1985, pp. 97 and 105), and a similar mechanism of action is recognized for dimethyl sulfoxide (Halliwell, B and Gutteridge, J M, 1985, pg. 147) and methionine (Del Maestro, R F, 1980, 164–165).

Several drug products containing PABA have been marketed for human use in the United States. Potassium p-aminobenzoate has been marketed as POTABA® in the pure form as an antifibrotic, i.e., skin softening agent (*Drug Information for the Health Care Professional,* 8th ed., 1988;, pgs. 111–113). As such it has been recognized for treatment of Peyronie's disease; diffuse systemic sclerosis; morphea and linear scleroderma; and dermatomyositis. For such purposes, POTABA® is taken orally in average doses of 12 grams/day for up to two years, although human use of 15–20 grams/day is recognized. As an ingredient in analgesic tablets, PABA has been marketed for domestic human use (300 mg/tablet) in PABIRIN® buffered tablets (with aspirin), in PABALATE® tablets (with sodium salicylate) and in PABALATE-SF® tablets (with potassium salicylate), as described in *Physicians's Desk Reference* (Huff, B B, 1980, pgs. 849, with aspirin and 1430, with salicylates).

In its summary on systemic use of PABA, the *Drug Information for the Health Care Professional* text (8th ed., 1988, pg. 111) presented the following statement (reproduced herein its entirety):

Mechanism of action: The mechanism by which aminobenzoate potassium exerts its antifibrotic effect is not known. It has been postulated that fibrosis results from an imbalance of serotonin and monoamine oxidase (MAO) mechanisms at the tissue level. Fibrosis is believed to occur when an excessive serotonin effect is sustained over a period of time. This could be the result of too much serotonin or too little MAO activity. Aminobenzoate potassium increases oxygen utilization at the tissue level. It has been suggested that this increased oxygen utilization could enhance the degradation of serotonin by enhancing MAO activity or other activities that decrease the tissue concentration of serotonin.

This inventor sees no relationship of such comments to the present invention, in particular, to the use of amine drugs in the treatment of chronic inflammatory disorders. Hence the clinical applications of compositions containing PABA claimed in this invention are recognized by the inventor as new and novel.

Certain amine agents have recognized anti-oxidant properties. These include N,N'-di-(sec-butyl)-p-phenylenediamine (Scott, G, 1965, pg. 120), aniline and aniline N-substituted agents (Scott, G, 1965, pg. 125). In the present invention, focus is placed on primary amine agents, as such agents are known to covalently react with carbonyl substances to yield Schiff base-type products (Feeney, RE et al., 1975, pg. 141). By contrast, N-substitution with hydrocarbon functional groups tends to increase amine anti-oxidant activity (Scott, G, 1965, pgs. 125 and 148). These are two distinct chemical phenomena. The anti-oxidant property of amines depends on their ability to act as electron donors to alkoxy or alkylperoxy radicals (Scott, G, 1965; pgs. 127, 145 and 158). The carbonyl trapping property of amines depends on their ability to form Schiff base-type addition products.

Vitamin C (ascorbic acid) is widely recognized as a water-soluble anti-oxidant vitamin. However, numerous published studies which have appeared since 1980 document that vitamin C also can act physiologically as a pro-oxidant (Gutteridge and Wilkins, 1982), an agent which stimulates lipid peroxidation (Chojkier et al., 1989, pgs. 16957 and 16961), and that it is a strong protein glycosylating agent (Ortwerth, B and Olesen, P, 1988, pgs. 12, 14, 16, 18 and 20). Thus, for example, in vitro studies have documented the ability of vitamin C to accelerate the process of cataract formation (Slight et al., 1990, pgs. 369–373). In addition, some evidence suggests that ascorbic acid may act as a factor which stimulates certain reactions which are characteristic of inflammatory diseases. For example, the presence of ascorbic acid in the synovial fluid of the arthritic joint may contribute to degradation of hyaluronic acid (Wong, S F et al., 1981; Higson, F K et al., 1988). For the purposes of the present disclosure, the hyaluronic acid present in the synovial fluid of the arthritic joint is defined as an example of the inflammation site structures that may reasonably be expected to be protected by use of the compositions of the present invention.

The use of dimethyl sulfoxide as a primary agent in combination with co-agents such as vitamins C, E, A, $B_1$, $B_5$, and $B_6$, as well as PABA, inositol, selenium, butylated hydroxytoluene, cysteine, thiodipropionates and zinc has been described for clinical treatment of arthritis (Pearson, D and Shaw, S, 1982, pp. 298). Dimethyl sulfoxide is clearly the primary agent of the composition disclosed on page 298 of Pearson and Shaw, as it is mentioned eight times. On line 27 of page 298, Pearson and Shaw disclose the preferred use of dimethyl sulfoxide in combination with anti-oxidant co-agents. Said anti-oxidant co-agents include PABA, which is mentioned only once on line 37. For the purposes of this disclosure, dimethyl sulfoxide is not included in any category of co-agent.

On page 299, Pearson and Shaw mention the singular use of vitamin $B_6$ in the treatment of arthritis, and on page 300 Pearson and Shaw advise the use of vitamin $B_6$ in combination with "other antioxidants" such as "vitamins A, E, B-5, C, and B-1, cysteine[,] zinc, selenium, inositol, choline, and PABA." Numerous other variations on this list of co-agents have been described publicly (e.g., Passwater, R A, 1985).

The disclosure of Pearson and Shaw contains several deficiencies which are resolved by the present invention. For example, they did not recognize the pro-oxidant, the lipid peroxidation stimulating or the protein glycosylating properties of vitamin C. While Pearson and Shaw (1982) refer repeatedly to vitamin C as the primary agent of their many compositions (e.g., pgs. 468–469 and 611–613), it is not the primary agent of the compositions and methods of the present invention.

Pearson and Shaw provide daily dosage ranges for composition ingredients on pages 468–469 and 611–613, and these sections clearly define excessively large doses vitamin C as the primary agent of their compositions. On page 469, Pearson and Shaw state a vitamin C daily dosage of from 3 to 10 grams, or from fifty to one hundred and sixty-six times the FDA RDA. On page 611, Pearson and Shaw state a vitamin C daily dosage of 20 grams, or three hundred and thirty-three times the FDA RDA. This clearly teaches away from the present disclosure.

Still further detracting from the idea of combining use of large amounts of vitamin C with PABA, under physiological conditions vitamin C readily degrades to dehydroascorbic acid (Sestili, M A, 1983). The ascorbic acid (i.e., vitamin C) molecule has one carbonyl group. Hence, it can form Schiff base derivatives with the primary agents of the present disclosure, substances such as PABA that contain primary amine functional groups in their structures. However, each molecule of dehydroascorbic acid has three carbonyl groups. These carbonyl groups can reasonably be expected to react with the primary amine functional group of PABA or other primary agents of the instant disclosure at physiological pH, and to whatever extent this may occur in vivo, the possible therapeutic value of the administered primary agent would be diminished.

Hence the prior art research studies noted above (e.g., Gutteridge and Wilkins, 1982; Chojkier et al., 1989, pgs. 16957 and 16961; Ortwerth, B and Olesen, P, 1988, pgs. 12, 14, 16, 18 and 20; Slight et al., 1990, pgs. 369–373; Wong, S F et al., 1981; and Higson, F K et al., 1988) indicate that systemic daily use of excessively large amounts of vitamin C as proposed by Pearson and Shaw may reasonably be expected to exacerbate the pathophysiological processes of the disease states addressed in the present Specification.

Furthermore,. as the reaction of the primary agents of the present invention with carbonyl substances generated by vitamin C-induced lipid peroxidation will limit the amount of primary agent available to sequester disease-related carbonyl substances otherwise present, the use of excessively large amounts of vitamin C can reasonably be expected to limit and diminish the possible therapeutic value of the presently disclosed PABA-based compositions.

Pearson and Shaw did not recognize the ability of carbonyl trapping agents such as PABA to chemically react with and sequester aldehydes and ketones which may result from and contribute to the non-enzymatic inflammatory cascade process. This inventive oversight on their part is of fundamental importance. This explains why Pearson and Shaw listed PABA only as one of many "anti-oxidant" and "membrane stabilizer" co-agents (see page 300).

Still further distinguishing the present disclosure from Pearson and Shaw, on pages 468 and 613 this prior art teaches the use of tryptophan, which is now banned by the FDA and is not contained within the limits of the present disclosure. In addition, Pearson and Shaw teach the combined use of L-dopa, vasopressin, Hydergine® and Deaner®, four prescription drugs. These prescription drugs are recited on pages 468–469 and pages 612–613 of Pearson and Shaw. These five substances are not part of the present disclosure, and were not part of the previous filings from which this disclosure has been derived.

Other co-agents disclosed by Pearson and Shaw, but not part of the present invention or the previous filings from which the present disclosure has been derived, include ribonucleic acid (RNA, pages 468 and 613) choline chloride (pages 468 and 613), L-arginine (pages 468 and 612), zinc gluconate (pages 468 and 612), sex hormones (page 469), thyroid extract (page 613), bromocriptine (page 613) and canthaxanthin (page 613). Having included such substances in the compositions of their disclosure, Pearson and Shaw offer no guidance as to how one ordinarily skilled in the art could proceed to selectively ignor such numerous distinctions so as to arrive at a prior art disclosure of the present invention.

Pearson and Shaw disclose on pages 468–469 a composition that contains twenty-six ingredients plus an optional twenty-seventh. The major ingredient (by weight) is vitamin C, 3–10 grams/day; followed by vitamin B-3, 3 grams/day; L-arginine, 3 grams/day; tryptophan, 2 grams/day; RNA, 2 grams/day; choline chloride, 1–3 grams/day; inositol, 1–3 grams/day; and then PABA, 1–2 grams/day. Hence PABA is the eighth major ingredient, followed by another eighteen or nineteen.

Pearson and Shaw disclose on pages 611–613 a composition that contains thirty-four ingredients. The major ingredient (by weight) is vitamin C, 20 grams/day; followed by vitamin E, 6 grams/day; ascorbyl palmitate, 3 grams/day; vitamin B-5, 3 grams/day; L-arginine, 3 grams/day; inositol, 5 or 17 grams/day; ornithine, 3 grams/day; choline chloride, 1–3 grams/day; and then PABA, 2 grams/day. Hence PABA is the ninth major ingredient, followed by another twenty-five. Having included such dosages in the methods of use of their compositions, Pearson and Shaw offer no guidance as to how one ordinarily skilled in the art could proceed to selectively ignor such numerous distinctions so as to arrive at a prior art disclosure of the present invention.

That one ordinarily skilled in the art might read Pearson and Shaw as anticipating the present disclosure is further contraindicated by the disclosure of Kessler (1990). In this handbook of publicly available nutritional products sold by Natural Organics, Inc., page 87 describes "a scientifically complete formulation based on recent research in the area of Life Extension by Durk Pearson., offering the fastest, most efficient, complete absorption and the ultimate results possible." This composition consists of twenty-five ingredients. In the stated dosage of five capsules, the major ingredient (by weight) is vitamin C, 1.25 grams; followed by inositol, 312.5 mg; L-cysteine, 250 mg; niacinamide, 240 mg; L-ornithine, 187.5 mg; ascorbyl palmitate, 187.5 mg; vitamin B-5, 187.5 mg; vitamin E, 200 mg; and then PABA, 125 mg. Hence PABA is the ninth major ingredient, followed by another sixteen. Other co-agents of the Kessler (1990, page 87) disclosure that are not part of the present invention or the previous filings from which the present disclosure has been derived, include ribonucleic acid, choline bitartrate, L-phenylalanine, rutin, hesperidin and zinc gluconate. This recitation by another party ordinarily skilled in the art confirms that Pearson and Shaw in fact did not offer guidance as to how one ordinarily skilled in the art could selectively interpret their work so as to arrive at the present invention.

Pearson and Shaw never disclose or anticipate a composition containing PABA as its primary agent, and in fact they teach away from such compositions. In contrast, PABA and derivatives thereof are identified as the required class of primary agents in the present invention, present in molar excess of any co-agent.

Zarafonetis (1953) has reported some success in treatment of rheumatoid arthritis by use of potassium p-aminobenzoate in combination with acetylsalicylic acid and cortisone. In this report Zarafonetis also described some success in clinical treatment of dermatomyositis and scleroderma by use of potassium p-aminobenzoate alone, and referred to earlier work on these disorders and other clinically related syndromes, including forms of lupus erythematosus.

Yet Zarafonetis based his logic for diversifying clinical studies on PABA or its potassium salt solely on similarities of clinical symptoms, comparisons among clinical syndromes which feature some common symptomology (Zarafonetis, 1953, pp 667–668; Zarafonetis, C J, 1964, pgs. 550 and 560; Priestley, G C and Brown, J C, 1979, pg. 161; Zarafonetis, C J et al., 1988, pg. 194). Zarafonetis never understood or recognized that PABA has the physiological potential of serving as a carbonyl chemical trapping agent (Zarafonetis, 1953, pg. 671). Hence, he never recognized its potential to sequester aldehyde and ketone products resulting from increased lipid peroxidation secondary to site-specific inflammation. In failing to recognize this principle, Zarafonetis failed to recognize the potential full scope of clinical applications of PABA. Failing to recognize the potential benefit of anti-oxidant co-agents, the procedures of Zarafonetis for treatment of scleroderma, rheumatoid arthritis and dermatomyositis relied on use of high PABA dosages (12–18 gm/day; see Zarafonetis, C J, 1953, pg. 666). In principle, the clinical prognosis of any disease featuring increased lipid peroxidation as part of its etiology can be improved by practice of the presently disclosed invention.

The 1953 Zarafonetis article states that patients with rheumatoid arthritis were initially treated with potassium p-aminobenzoate (KPAB) and cortisone. The first patient treated with this combination of agents responded well, but unknown to the author, this patient was also taking aspirin. When this fact was discovered and the aspirin was discontinued, a definite relapse occurred. Improvement reappeared upon its resumption (page 670, right column, lines 9–15 following heading "Rheumatoid Arthritis"). After much trial, Zarafonetis settled on a tentative treatment of 12 grams of KPAB daily in six doses of 2 grams each, and 2.4 grams of aspirin in four doses of 600 mg each (page 666, right column, lines 31–37). The author also stated that the mechanism of action of KPAB, the potassium salt of PABA is unknown (page 671, right column, line 20). Zarafonetis provides no instruction on the possibility of combining PABA or KPAB with anything other than aspirin or cortisone.

Zarafonetis (1953) also referred to an earlier study which used a combination of p-aminobenzoic acid and α-tocopherol to treat scleroderma. Gougerot and Hewitt (1951) described the logic of their scleroderma treatment protocol as follows:

This observation is to be added to the file of the treatment of sclerodermas. Zarafonetis and his collaborators have already published 5 cases of sclerodermas improved by para-amino-benzoic acid, and in the same therapeutic series Shaffer and his collaborators treated a generalized scleroderma with para-aminobenzoic acid with improvement. In a study of a completely different nature, vitamin E (a-tocopherol) was used by Klemperer, etc. and in France by Bazex (Lyon, July 1949). This is why we have associated the two therapies because of their effect on diseases of collagen.

As such, they perceived their clinical treatment strategy to address the status of collagen, with no discussion of possible physiological mechanisms. Compared to the present invention, Gougerot and Hewitt:

(1) used a dosage method that is not claimed in the present invention, namely 1.75 gm of PABA daily, optionally in combination with a co-agent of 30 mg vitamin E daily;

(2) failed to recognize that either of their therapeutic agents may interfere with the non-enzymatic inflammatory cascade;

(3) failed to recognize that primary amine and amine-related derivatives of benzoic acid, as a class, may bind to and sequester aldehydes which result from the inflammatory process; and (4) failed to understand that the combination of a water soluble aldehyde-trapping primary amine agent and a lipophilic anti-oxidant co-agent may have clinical application to the treatment of a broad spectrum of chronic inflammatory disorders.

Gougerot and Hewitt teaches a composition of PABA which is adapted for bimodal administration (oral, 0.75 gram and intravenous, 1.0 gram) in which the major amount of PABA. is administered by injection. This combination of routes of administration is burdensome and impractical for the patient, an d thus can reasonably be expected to encourage therapeutic protocol noncompliance or eventual abandonment of the therapeutic procedure. Administration of primary agents or co-agents via injection, in whole or in part, lies completely beyond the scope of the present invention.

In addition, it should be noted that while the present invention requires ongoing daily treatment, the procedure of Gougerot and Hewitt did not. Gougerot and Hewitt teaches the treatment of scleroderma in a series of three treatment periods, with intervening periods in which no treatment is provided. According to Gougerot and Hewitt, treatment period one in April 1950 consisted of 20 days of daily administration of PABA by a combination of injection and oral routes, with no co-agent. The method of singular use of PABA lies completely beyond the limits of the present invention, as does its bimodal administration. Treatment period two in June 1950 consisted of 20 days of daily administration of PABA by a combination of injection and oral routes, in combination with 30 mg daily of vitamin E as an oral co-agent. Treatment period three in September 1950 consisted of the same protocol as treatment period two. Both the daily dosage amount of PABA and that of vitamin E lie below the disclosed ranges of use of the present invention. Hence, Gougerot and Hewitt disclosed a composition optionally containing one co-agent in combination with PABA (treatments two and three) or containing no co-agent whatsoever (treatment period one). This optional presence of the co-agent in the composition, regardless of the nature of the co-agent, lies fundamentally beyond the limits of the present invention.

Furthermore, the intermittent nature of the method of Gougerot and Hewitt disclosure lies beyond the scope of the present invention. During the total period of observation reported by Gougerot and Hewitt, from April to December 1950, no treatment whatsoever was provided in May, July, August, October, November and December. Such a sporadic treatment protocol lies entirely beyond the perview of the instant disclosure, and in fact teaches away from the ongoing daily treatment methodology and compositions defined in the present Specification.

Broad spectrum clinical use of anti-inflammatory vitamin compositions which feature PABA as the primary agent, and the methodological reasoning for doing so, has not been previously recognized or described. p-Aminobenzoic acid is not presently recognized as a non-steroidal anti-inflammatory drug (NSAID). Hence, for example, it is not included in the lists of such drugs published in (a) the *Merck Index,* (Budavari, S, 1989, pages THER-15 to THER-16), (b) *Scientific American* (Weissmann, G, 1991, page 86), and (c) *Understanding Arthritis* (Kushner, I, 1984, pages 52–53). Likewise, p-aminobenzoic acid is not recognized as being a "slow acting" anti-inflammatory agent (*Understanding Arthritis,* Kushner, I, 1984, pages 55–57).

SUMMARY OF THE INVENTION

These and other objects of this invention are achieved by providing a novel method and compositions for clinical treatment of chronic inflammatory disorders. This invention involves use of orally administered primary amine derivatives of benzoic acid and partially or fully saturated analogs or precursors thereof capable of hydrolyzing to the primary amine derivative, for example amides, as carbonyl trapping agents. These are the primary agents of the presently disclosed compositions and methods. They act by chemically binding to and sequestering the aldehyde and/or ketone products of lipid peroxidation. Increased levels of lipid peroxidation have been repeatedly demonstrated as a part of the non-enzymatic inflammatory cascade process which underlies the secondary etiology of chronic inflammatory diseases. p-Aminobenzoic acid ,is an example of the primary agent of the present invention. PABA has a small molecular weight, is water soluble, has a primary amine functional group which reacts with carbonyl-containing metabolites under physiological conditions and is tolerated by the body in relatively high dosages and for extended periods.

The present invention is directed to the oral use of primary agents that are carbonyl sequestering substances administered in combination with co-agents selected from the group consisting of clinically effective anti-oxidants and free radical trapping compounds (e.g., α-tocopherol), compounds having indirect anti-oxidant activity (e.g., selenium), vitamins (e.g., pyridoxine HCl), compounds which facilitate kidney drug elimination (e.g., glycine), metabolites at risk of depletion (e.g., pantothenic acid), sulfhydryl containing chemicals (e.g., methionine), compounds which facilitate glutathione activity (e.g., N-acetylcysteine), and non-absorbable polyamine co-agents (e.g., chitosan).

1. Aims of the Invention

Accordingly, it is a general object of this invention to treat chronic inflammatory disorders by oral use of compositions of primary agents that are carbonyl trapping agents in combination with clinically effective anti-oxidant and lipid peroxidation inhibitor co-agents so as to create compositions with additive, complementary physiological therapeutic characteristics. It is a further object of this invention to use orally consumed substances that are co-agents which have indirect anti-oxidant activity, vitamin co-agents, co-agents which facilitate kidney drug elimination, co-agents which are metabolites at risk of depletion, and co-agents which are sulfhydryl containing chemicals, and co-agents which facilitate glutathione activity. It is a further object of this invention to use orally consumed co-agents which are of a non-digestible nature that are carbonyl trapping substances possessing primary amine functional groups, so as to bind and sequester carbonyl chemical agents that are present in food and thus prevent such toxic agents from being absorbed into the body.

2. Statement of Invention

The method of the present invention uses primary agents that are carbonyl trapping substances such as derivatives of benzoic acid that contain primary amine functional groups or partly or fully saturated analogs thereof or precursors thereof capable of hydrolyzing to the primary amine functional group derivative, for example amides, to treat chronic inflammatory disorders. The further use of said primary agents in combination with anti-oxidant free radical trapping agents can reasonably be expected to produce improved therapeutic properties.

It is known that aldehyde chemical metabolites, which contain carbonyl functional groups, are generated during the process of chronic inflammation. These aldehyde products result from the degradation of unsaturated fatty acids in the course of pathologically increased lipid peroxidation, which may be initiated by a variety of activated oxygen chemical species such as the hydroxyl radical, HO (Halliwell, B and Gutteridge, J M, 1985, pp. 119–120). The reactive cascade of free radical propagation → lipid peroxidation → aldehyde formation and other subsequent effects of inflammation is well documented in the prior art (Halliwell, B and Gutteridge, J M, 1985, pp. 102–103). This pathophysiological process is referred to herein as the nonenzymatic inflammatory cascade. Aldehyde products of this reactive cascade are known to react with free amino groups of proteins, nucleic acids and phospholipids to form Schiff bases (Hatherill, J R et al., 1991, pg. 352). The many resulting toxic fatty aldehyde products include malondialdehyde, 4,5-dihydroxydecenal and 4-hydroxy-2,3-trans-nonenal (Esterbauer, H et al., 1982; Halliwell, B and Gutteridge, J M, 1985, pp. 123; Dowling, E J et al., 1987).

In addition, some of these aldehydes function as chemotactic agents (Curzio M et al., 1986; Rossi M A et al., 1993; Curzio M et al., 1994). As such, they effectively attract white blood cells to sites of inflammation. Once attracted by such a mechanism, white blood cells release activated oxygen chemical species, thereby exacerbating an inflammatory process (Fantone, J C, Ward, P A, 1982).

Previously, attempts at pharmaceutical intervention in this cascade of inflammatory reactions has focused primarily on use of both water-soluble and lipid-soluble anti-oxidant free radical trapping agents or use of metal chelating agents (Halliwell, B and Gutteridge, J M, 1985, pp. 125 and 116–117). As iron and copper ions have been shown to induce hydroxyl radical formation (Halliwell, B and Gutteridge, J M, 1985, pg. 123) and induce lipid peroxidation (Halliwell, B and Gutteridge, J M, 1985, pg. 124), the use of metal chelating agents such as desferrioxamine to ameliorate the inflammatory cascade has received some attention (Halliwell, B and Gutteridge, J M, 1985, pp. 116–117). However, desferrioxamine has predictable ocular and auditory side effects (Halliwell, B and Gutteridge, J M, 1985, pgs. 117 and 140), and present examples of anti-oxidant free radical trapping agents and combinations thereof have proven to be of limited clinical value.

Both PABA and D-penicillamine are primary amine agents which also function as anti-oxidant free radical trapping agents. Yet as anti-oxidant agents PABA and D-penicillamine are presently regarded as being of secondary, nominal value, due either to weak anti-oxidant properties or toxic side effects, respectively. Thus their use as anti-inflammatory agents has been quite limited. Their potential value for trapping the aldehyde products of inflammation-related lipid peroxidation has never been recognized. Hence the formulation of a new orally administered composition, such as one having PABA as its primary agent, and a clincally effective anti-oxidant free radical scavenging chemical in a presently claimed dosage range as co-agent, has never been previously described, and the potential for clinical use solely via the oral route of administration of such a novel composition in treatment of chronic inflammatory disorders never recognized.

The present invention is based on use of primary amine derivatives of benzoic acid and their partially or fully saturated analogs and precursors thereof as principle agents for chemically binding to and sequestering aldehyde products of inflammation site lipid peroxidation, and their use, in part, in combination with clinically effective anti-oxidant free radical trapping co-agents. This unique, multiple-level approach to interference with certain steps in the inflammatory cascade has not been previously recognized by other research investigators. This is, in fact, the first anti-inflammatory agent composition invention which addresses the issue of aldehyde formation at inflammation sites. As aldehydes are highly reactive molecules capable of reacting with proteins, lipids and nucleic acids (Jellum, E et al., 1973, pg. 200; Carden, M J et al., 1986; Halliwell, B and Gutteridge, J M, 1985, pg. 123), their increased formation at inflammation sites may be a significant contributing factor in the evolution of the clinical pathology of inflammatory disorders. Said inflammation site proteins, lipids and nucleic acids are further examples of the inflammatory site structures to be protected by the practice of the present invention.

The results of several published research studies indicate that increased lipid peroxidation is a contributing factor in the etiologies of a variety of chronic inflammatory diseases, such as rheumatoid arthritis (Muus, P et al., 1979; Rowley, D et al., 1984; Selley, M L 1992; Jasin, H E, 1993; Winyard, P G et al., 1993; Mapp, P I et al., 1995), multiple sclerosis (Hunter, M I et al., 1985; Halliwell, B and Gutteridge, J M, 1985, pg. 125; Calabrese, V et al., 1994), repetitive stress injury (Lukoschek, M et al., 1990; Pitner, M A, 1990), colitis (Tamai, H et al., 1992) and chronic inflammatory bowel disease (Ahnfelt-Ronne, I et al., 1990; Gross, V et al., 1994; McKenzie, S J et al., 1996).

Furthermore, the results of several published research studies indicate that increased lipid peroxidation is a contributing factor in the etiologies of Duchenne muscular dystrophy (Kar, N C and Pearson, C M, 1979; Jackson, M J et al., 1984; Halliwell, B and Gutteridge, J M, 1985, pg. 125) and silicosis (Katsnelson, B A et al., 1989, pg. 318). As exposure to asbestos fibers can stimulate lipid peroxidation (Halliwell, B and Gutteridge, J M, 1985, pg. 152), asbestbsis should also be included in this category. Increased lipid peroxidation has also been demonstrated in acute post-event central nervous system trauma (Hall, E D, 1987, pgs. 421 and 424; Demopoulos, H B et al., 1980, pg. 97; Kontos, H A et al., 1981, pg. 2329), as a result of stroke (Zivin, J A and Choi, D W, 1991, pg. 61) and subsequent to myocardial infarction (Kurdin, A N, 1978; Pucheu, S et al., 1995). Status epilepticus is one of several clinical disorders which have been linked to increased intracellular concentrations of free radicals, with subsequent lipid peroxidation (Del Maestro, R F, 1980, pg. 163). Likewise, published evidence has documented the ability of carbonyl compounds resulting from lipid peroxidation to induce foot edema in the rat (Benedetti, A et al., 1980).

Hence, within the context of the present invention and because of a commonly shared element of pathophysiology characterized by increased lipid peroxidation, the following disease states are presently included in the subject category of chronic inflammatory disorders: chronic gingivitis, chronic periodontitis, chronic autoimmune gastritis, ileitis, colitis, interstitial cystitis, arthritis, tendinitis, cumulative trauma disorders, systemic lupus erythematosus, autoimmune vasculitis, asbestosis, silicosis, Lyme disease, inflammatory myopathies, Duchenne muscular dystrophy, epilepsy, inflammatory neuropathies, myasthenia gravis, multiple sclerosis, inflammatory site edema, post-event acute central nervous system trauma, stroke, and myocardial infarction.

DETAILED DESCRIPTION OF THE PREFERRED EMBODIMENT

It is understood that the therapeutically effective dosage ranges of co-agents disclosed below apply to use by adult human subjects, and that such dosage ranges can be adapted on a kilogram body weight basis (assuming adult human weight from 45 kg to 136 kg) to use by non-adult humans or veterinary mammalian subjects.

The points of novelty and utility of this invention are (1) the disclosure of compositions consisting of primary agents which are absorbable carbonyl trapping drugs in combination with co-agents which may reasonably be expected to increase the therapeutic value of the primary agents and (2) the defined use of said compositions when administered by the oral route to a mammalian subject for treatment of chronic inflammatory disorders. As defined herein, administration is limited to the oral route.

In a preferred embodiment, the therapeutically effective amount of the primary agent of the present invention for the mammalian subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day.

In another preferred embodiment, use of a primary agent in combination with a clinically effective anti-oxidant and lipid peroxidation inhibitor co-agent may be of particular benefit in preventing or ameliorating forms of chronic inflammation by incorporating two pharmacological strategies, the sequestering of cytotoxic aldehydes and ketones generated at sites of chronic inflammation and the sequestering of activated oxygen chemical species generated earlier in the non-enzymatic inflammatory cascade.

In another preferred embodiment, it is further understood that concomitant oral use of one or more co-agents having indirect anti-oxidant activity, vitamin co-agents, co-agents which facilitate kidney drug elimination, co-agents which are metabolites at risk of depletion, sulfhydryl compound co-agents, or co-agent compounds which facilitate glutathione activity may complement the intended therapeutic results.

In another preferred embodiment, it is further understood that concomitant oral use of non-digestible polyamine carbonyl trapping co-agents may serve to prevent absorption of dietary aldehydes and ketones from the alimentary tract into the body, thus complementing the intended therapeutic results and benefiting the mammalian subject.

In another preferred embodiment, the therapeutically effective amount of the non-digestible polyamine co-agent of the present invention for the mammalian subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day.

(i) Mechanism of Action of Primary Agents

The pharmacological reactions of the present invention are based on the ability of primary amine compounds to react with aldehyde functional groups of potentially toxic agents, yielding covalently bound Schiff base products. Several examples of chemically analogous reactions, presented within other contexts, have been publicly presented. Representative examples are discussed below. These model chemical systems are directly analogous to the proposed mechanism of drug action of the primary agents of the present invention.

Comments by Feeney and coworkers (1975, pg. 141) provide an appropriate introduction to this subject:

A wide variety of substances with —NH$_2$ groups condense with carbonyl compounds . . . This condensation of primary amines with aldehydes and ketones to give imines was first discovered by Schiff (1900). The overall equilibrium greatly favors hydrolysis in aqueous solution for aliphatic aldehydes. With aromatic aldehydes, the equilibrium is shifted in favor of Schiff base formation. It is important to note that increasing the nucleophilic strength of the amine will increase the rate of the carbonylamine reaction but will have almost no effect on the position of the equilibrium.

These comments suggest that the amine-containing carbonyl-trapping drugs that are the primary agents described herein should have particular promise for binding furanaldehydes, which are aromatic. These comments also suggest that doses of primary agent absorbable amine drugs may require in vivo concentrations in the range of 1:100 to 1:1,000 (carbonyl:amine) in order to achieve clinical effectiveness. This, in turn, suggests that therapeutic dosages for adult human subjects lie in the range of grams per day and that only drugs of particularly low toxicity will have human applications.

Feeney and coworkers (1975, pg. 144) also noted the phenomenon of Schiff base transimination, which occurs to a significant extent at neutral pH:

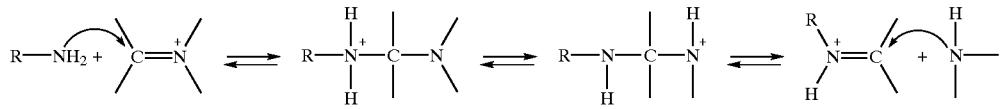

The existence of such non-enzymatic reversible transimination reactions is important within the context of this invention, as it suggests that in vivo both bound carbonyl agents, in addition to free carbonyl agents, may be sequestered by amine-containing drugs.

(a) The direct in vitro addition of p-aminobenzoic acid or ethyl p-aminobenzoate to malondialdehyde or its tautomer, β-hydroxy-acrolein, has been described (Sawicki, E et al., 1963).

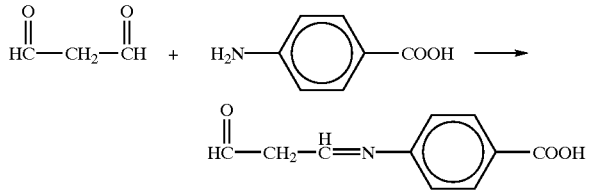

The metabolic fate of PABA in humans has been actively investigated and well reported in the biomedical literature (Young, D S et al., 1971; Howie, M B and Bourke, E, 1979). It is so actively metabolized via several mechanisms and quantitatively removed in urine (Weizman, Z et al., 1985; Bingham, S and Cummings, J H, 1983) that PABA excretion has become a widely recognized standard for measuring urinary clearance. Small amounts of PABA are normally present in the human diet. It is recognized as being a vitamin for many organisms and is classified as a member of the vitamin B complex (Smith, W T, 1976, pg. 194; Winitz, M et al., 1970, pgs. 527–528; Scott, C C and Robbins, E B, 1942). As a vitamin for human use PABA is commercially marketed in the dosage range of 5 to 550 mg/day.

(b) The direct in vitro addition of n-hexylamine to β-hydroxy-acrolein to produce an N,N'-disubstituted 1-amino-3-iminopropene derivative has been reported (Chio, K S and Tappel, A L, 1969). The reaction may be represented as follows:

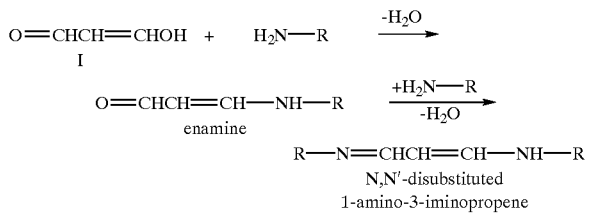

(c) The direct chemical addition of amines to 5-methyl-2-furfural has been described, (Holdren, R F and Hixon, R M, 1946). A wide variety of aliphatic and aromatic primary amines can add to furfural in this manner, yielding Shiff base products (Dunlop, A P and Peters, F N, 1953, pg. 353).

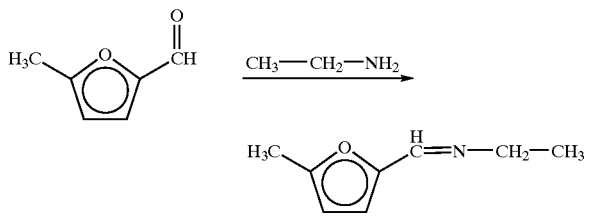

(d) As described by Dunlop and Peters (1953, pg. 373) earlier work demonstrated the ability of furfural to react with amino-sulfonic salts to produce furfurylideneaminosulfonates:

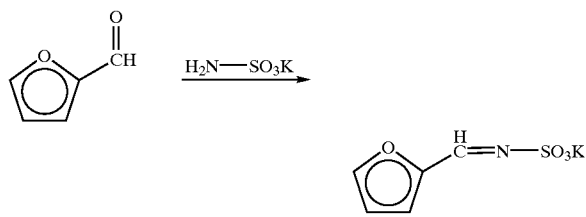

(e) The reaction of phenylaminoguanidine with furfural (Dunlop, A P and Peters, F N, 1953, pg. 371) may serve as an example of covalent furanaldehyde trapping with a hydrazine.

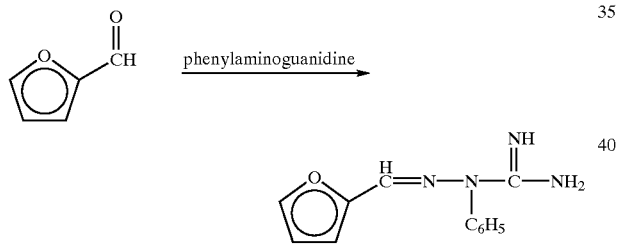

(f) Self-polymerization of o-aminobenzaldehyde has been described. In the 1994 edition of the Sigma Chemical Company catalog of biochemical reagents the following statement appears on page 90 of its listing: "o-AMINOBENZALDEHYDE Unstable! [store at] −20 C. Polymerizes rapidly when exposed to room temperature. May yield slightly hazy solution in ethanol due to presence of a small amount of polymer. Shipped in dry ice." This information directly indicates that a primary amino group covalently linked to a benzene ring possesses sufficient reactivity for significant reaction with aldehyde functional groups at room temperature. It is apparent that no form of activation of the amino group is required and that a Schiff base product forms readily.

The small molecular weight, absorbable, primary amine-containing drugs and amine-related drugs to be administered via the oral route as primary agents described herein have analogous behavior in vivo, as well as an additional characteristic which will facilitate disposal as urine metabolites. All of these drugs contain a carboxylic acid group to facilitate uptake and processing by the kidneys.

(ii) Examples of Primary Agents

This invention is limited to compositions that include at least one primary agent as defined in the present section in required combination with one or more anti-oxidant and free radical trapping co-agents, co-agents having indirect anti-oxidant activity, vitamin co-agents, co-agents which facilitate kidney drug elimination, co-agents which are metabolites at risk of depletion, sulfhydryl co-agents, co-agents which may facilitate glutathione activity, or non-absorbable primary amine co-agents, and use thereof via the oral route. Said classes of co-agents are defined in subsequent sections below. For any primary agent listed herein as useful in the present invention, its precursors in the form of pharmaceutically acceptable salts, pharmaceutically acceptable esters and pharmaceutically acceptable amide derivatives thereof will also be useful. The class of primary agents (molecular weight range 100 to 1,400) of the present invention may be summarized as a compound of the formula

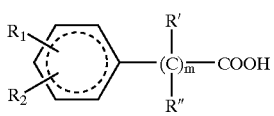

wherein the 6-membered ring is phenyl, cyclohexadienene, cyclohexene or cyclohexane; and wherein $R_1$ is —$NH_2$; aminoalkyl- having 1–10 carbons; —NHC(=NH)$NH_2$;
—$(CH_2)_n$NHC(=NH)$NH_2$ wherein n is 1–10;
—C(=NH)$NH_2$;
—$(CH_2)_n$—CH=NC(=NH)$NH_2$ wherein n is 1–10;
—NHC(=NH)NH$NH_2$;
—$(CH_2)_n$NHC(=NH)NH$NH_2$ wherein n is 1–10;
—$(CH_2)_n$—CH=NC(=NH)NH$NH_2$ wherein n is 1–10;
—NHNHC(=NH)$NH_2$; —$(CH_2)_n$—NHNHC(=NH)$NH_2$ wherein n is 1–10;
or —$(CH_2)_n$—CH=N—NHC(=NH)$NH_2$ wherein n is 1–10;

$R_2$ is H; —OH; —O—$CH_3$; —O—R wherein R is alkyl of 2–10 carbons; aminoalkyl wherein the alkyl group is 1–10 carbons; —$SO_3$H; —$CH_3$; and —$(CH_2)_n CH_3$ wherein n is 1–10;

R' and R" are —H, OH or $CH_3$; and m is 0 or 1.

For purposes of this invention, a therapeutically effective amount of the primary agent for a mammalian subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day.

(iii) Mechanism of Action of Non-Digestible Polyamine Co-Agents

The presence of aldehydes and ketones in the human diet also is a factor which may put the patient suffering from a chronic inflammatory disease further at risk. This can be especially important for victims of ileitis and colitis, as the damaging effects of inflammation site carbonyl compounds may be accentuated by direct exposure to dietary carbonyl agents. 5-Methyl furfural has been identified in the oil of roasted coffee and in oil of cloves (Dunlop, A P and Peters, F N, 1953, pg. 403). 5-Hydroxymethyl furfural has been found in sherry, port and brandy alcoholic beverages; honey and other sugar syrup products (Lever, M et al., 1985). Levels of furfural (i.e., 2-furanaldehyde or 2-furancarboxaldehyde) and 5-hydroxymethyl-2-furanaldehyde (i.e., 5-hydroxymethyl furfural) as high as 4.5 mg/L and 93.2 mg/L, respectively, have been found in wine products (Shimizu, J and Watanabe, M, 1979). Furfural has also been detected in beer and distilled liquors (Dunlop, A P and Peters, F N, 1953, pg. 308), as well as in natural oil products such as oil of lime (Dunlop, A P and Peters, F N, 1953, pg. 280). Summarizing earlier work, Rice (1972) noted:

> Small quantities of furfural occur in many foodstuffs, including—among many others—bread, coffee, processed fruits and fruit juices, and alcoholic beverages. In fact, whenever plant or animal tissue containing pentoses or hexoses is subjected to heat, the possibility arises that furfural, 5-hydroxymethyl furfural, and probably other furans as well will be produced.

Pettersen and Jellum (1972) referred to earlier work which demonstrated the generation of 2-furanaldehyde, 5-hydroxymethyl-2-furanaldehyde and 2,5-furandicarboxaldehyde during bread baking. In his food chemistry study, Baltes (1985) noted the presence of furfural in curing smoke tar; and the presence of furfural, 5-methyl-2-furfural, dihydrofuranone, 5-hydroxymethyl-2-furfural and 2,5-furandialdehyde in caramels. Baltes also examined the products obtained by Maillard reaction of glucose and phenylalanine and identified furfural and 2,5-di-(hydroxymethyl)-furan among the main components. Thus various furan aldehyde compounds have been identified in the human diet.

In addition, a wide variety of naturally occurring non-aromatic and aromatic aldehydes and ketones have been found in fruits and vegetables (Schauenstein, E and Esterbauer, H, 1977, pgs. 181–194). These include alkanals, alk-2,4-dienals, alk-2-enals, alk-1-en-3-ones, α-dicarbonyl compounds, β-dicarbonyl compounds alkan-2-ones. Schauenstein and Esterbauer have noted, in part, that:

> Aliphatic carbonyl compounds represent the most important group of flavouring compounds in our foodstuffs. One finds them in all flavour extracts. They are either entirely, or in large measure, responsible for nearly all known flavours and determine, even when present in small amounts, the taste and odour of our foodstuffs, and beverages such as tea and coffee . . . (pg. 189)

As the presence of carbonyl agents in the diet is not restricted to fruits and vegetables, Schauenstein and Estabauer have further noted that:

> Unsaturated aldehydes also arise through thermal degradation of carbohydrates, amino acids, and fats. Such thermal degradative processes are probably responsible for the presence of these aldehydes in boiled, fried, and baked foods. Unsaturated aldehydes have been detected in a large number of foodstuffs, such as potatoes, potato chips, poultry, meat, fish, salad oils, bread, and bakery products . . . (pgs. 193–194)

As such, it is apparent that the diet is a significant source of carbonyl agents, and their presence may be a contributing factor in the etiology of chronic inflammatory diseases. Toxic properties of furanaldehyde derivatives have been demonstrated in both in vivo and in vitro studies (Konecki, J et al., 1974; Ulbricht, R J et al., 1984). Non-digestible polyamine-containing co-agents such as those defined below can be of health benefit by virtue of their ability to covalently trap dietary aldehydes and ketones. The co-agents described in this section can accomplish this function because they bear primary amine groups. As large molecular weight molecules which are non-digestible they have the capacity to pass through the digestive tract, acting in effect as another form of dietary fiber. These non-absorbable carbonyl trapping substances may include naturally occurring polyamine polysaccharides, chemical derivatives of naturally occurring polysaccharides, and synthetic polyamine polymers. The fate of malondialdehyde (MDA) given orally to rats may serve as an example of the metabolism of dietary aldehydes, and how an understanding of this process can be used to define non-absorbable carbonyl-trapping co-agents. Studies by Draper and coworkers (1986) demonstrated that the primary form of "bound" MDA in rat or human urine is N-α-acetyl-ε-(2-propenal)lysine. This is the biologically acetylated derivative of the MDA-lysine adduct N-ε-(2-propenal)lysine, as shown below.

Draper and coworkers (1986) were able to generate N-ε-(2-propenal)-lysine in vitro by exposing beef muscle protein to MDA, followed by treatment with pepsin and hog intestinal juice. This indicates that the ε-amino groups of dietary protein lysine

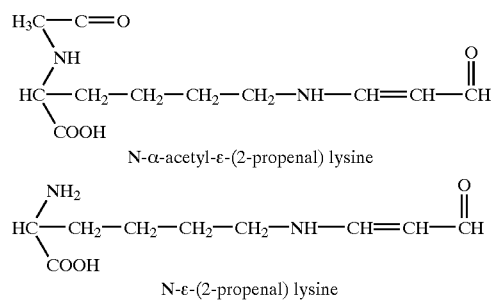

N-α-acetyl-ε-(2-propenal) lysine

N-ε-(2-propenal) lysine residues can covalently bind dietary aldehyde under conditions found in the intestinal tract. As such, chemically analogous primary amine groups on the non-absorbable co-agents of the present invention also are capable of covalently binding dietary aldehydes under conditions to be found in the intestinal tract. In this case, however, the bound carbonyl species are excreted in the feces, thus preventing subsequent in vivo exposure to dietary carbonyl agents.

In their study Draper and coworkers noted that N-α-acetyl-ε-(2-propenal)lysine was found in urine of fasted rats or animals fed on MDA-free diets, indicating that the MDA-lysine adduct also forms in vivo. These investigators referred to earlier work which demonstrated that the MDA concentration normally found in food is in the range of <0.1 to 10 ppm (0.1 to 10 $\mu$M), which gives some idea of dietary aldehyde concentrations.

(iv) Examples of Orally Administered Non-Digestible Polyamine Co-Agents Useful in the Method of the Present Invention The orally administered compositions of the present invention include at least one primary agent as defined above in section (ii) in combination with at least one co-agent selected from the group consisting of anti-oxidant and free radical trapping compounds, compounds having indirect anti-oxidant activity, vitamins, compounds which facilitate kidney drug elimination, metabolites at risk of depletion, sulfhydryl compounds, and compounds which facilitate glutathione activity. In addition, compositions of the present invention may optionally include non-digestible polyamine co-agents. Said non-digestible polyamine co-agents are not absorbable in the gastrointestinal tract due to their large molecular weights and chemical structures resistant to hydrolysis. Said non-digestible polyamine co-agents selected from the following group.

a. Naturally Occurring Amine-Containing Polysaccharides. Any naturally occurring polysaccharide featuring β-1, 2, β-1,3, β-1,4 and/or β-1,6 linkages which contains aminosugars may be regarded as a non-digestible, potentially active carbonyl trapping agent. The chitin class of biopolymers may be cited as an example of such an agent, having the general structure of poly-β-(1→4)-N-acetyl-D-glucosamine A form of microcrystalline chitin has been described in which some of the acetyl groups have been removed, revealing free amine groups (Austin and coworkers, 1981, pg. 750). Chitins obtained from different sources feature different degrees of amine deacetylation (Austin and coworkers, 1981, pg. 752).

b. Deacetylation of Naturally Occurring Polysaccharides. Various pretreatment procedures may be applied to naturally occurring polysaccharides prior to generation of chemical derivatives. Generation of microcrystalline polysaccharides is one example of such a pretreatment procedure. As applied to cellulose or chitin (Yalpani, 1988, pg. 389), this yields a colloidal processed form of polysaccharide featuring high porosity and enhanced susceptibility to chemical reactions. Generation of "microfibrillated" cellulose or chitin is another example of a pretreatment procedure which produces enhanced surface area, increased water retention capacity and enhanced chemical accessibility (Yalpani, 1988, pg. 390). Use of strong (>18%) sodium hydroxide is still another recognized pretreatment, or activation, procedure found to be helpful as a starting point for preparing chemical derivatives of polysaccharides (Yalpani, 1988, pg. 214). A variety of polysaccharides have been identified which are rich in N-acetylated residues. Upon chemical deacetylation these carbohydrates yield high molecular weight derivatives bearing primary amine groups directly linked to sugar carbons, that is, no sidearm spacer units present. This group includes, but is not limited to, chitosan.

c. Chemically aminated polysaccharides selected from the group consisting of:
  aminodeoxy polysaccharides including 2-amino-2-deoxy cellulose; amino alkyl-, amino(hydroxyalkyl)-, aminoalkyl-ether-, and amino(hydroxyalkyl)-ether- derivatives of cellulose, chitin and other naturally occurring non-digestible carbohydrates selected from the group consisting of
    $H_2N$—$(CH_2)_n$-[carbohydrate] where n=1–10, including alkyl isomers;.
    $H_2N$—$(CH_2)_m$—CHOH—$(CH_2)_n$-[carbohydrate], where m=0–10 and n=0–10;
    $H_2N$—$(CH_2)_n$—O-[carbohydrate] where n=1–10;
    $H_2N$—$(CH_2)_{mf}$—CHOH—$(CH_2)_n$—O-[carbohydrate] where m=0–10 and n=0–10;
  aminobenzyl derivatives of cellulose, chitin or other naturally occurring non-digestible carbohydrates selected from the group consisting of
    $H_2N$—$C_6H_4$—$(CH_2)_n$-[carbohydrate],
    $H_2N$—$CH_2$—$C_6H_4$—$(CH_2)_n$-[carbohydrate],
    $H_2N$—$C_6H_4$—$(CH_2)_n$—O-[carbohydrate] where n=0–10, and
    $H_2N$—$C_6H_4$—$(CH_2)_m$—CHOH—$(CH_2)_n$-O—[carbohydrate] where m=0–10 and n=0–10, including p-, o- and m-benzene ring amino- isomers, aminomethyl- isomers and alkyl group isomers thereof;
  guanidine and aminoguanidine derivatives of cellulose, chitin or other naturally occurring non-absorbable carbohydrates selected from the group consisting of:
    $H_2N$—C(=NH)-[carbohydrate];
    $H_2N$—C(=NH)—$(CH_2)_n$-[carbohydrate], where n=1–10, including hydrocarbon isomers and hydroxylated derivatives thereof;
    $H_2N$—C(=NH)—O—$(CH_2)_n$-[carbohydrate], where n=1–10, including hydrocarbon isomers, ether linkage isomers and hydroxylated derivatives thereof;
    $H_2N$—C(=NH)—NH-[carbohydrate];
    $H_2N$—C(=NH)—NH—$(CH_2)_n$-[carbohydrate], where n=1–10, including hydrocarbon isomers and hydroxylated derivatives thereof;
    $H_2N$—C(=NH)—NH—$(CH_2)_n$—O-[carbohydrate], where n=1–10, including hydrocarbon isomers, ether linkage isomers and hydroxylated derivatives thereof;
    $H_2N$—C(=NH)—N=CH—$(CH_2)_n$-[carbohydrate], where n=1–10, including hydrocarbon isomers and hydroxylated derivatives thereof;
    $H_2N$—C(=NH)—N=CH—$(CH_2)_n$—O-[carbohydrate], where n=1–10, including hydrocarbon isomers and hydroxylated derivatives thereof;
    $H_2N$—NHC(=NH)—NH-[carbohydrate ];
    $H_2N$—NHC(=NH)—NH—$(CH_2)_n$-[carbohydrate], where n=1–10, including hydrocarbon isomers and hydroxylated derivatives thereof;
    $H_2N$—NHC(=NH)—NH—$(CH_2)_n$—O-[carbohydrate], where n=1–10, including hydrocarbon isomers, ether linkage isomers and hydroxylated derivatives thereof;
    $H_2N$—NHC(=NH)—N=CH—$(CH_2)_n$-[carbohydrate], where n=1–10, including hydrocarbon isomers and hydroxylated derivatives thereof;
    $H_2N$—NHC(=NH)—N=CH—$(CH_2)_n$—O-[carbohydrate], where n 1–10, including hydrocarbon isomers, ether linkage isomers and hydroxylated derivatives thereof;
    $H_2N$—C(=NH)—NH—NH-[carbohydrate];
    $H_2N$—C(=NH)—NH—NH—$(CH_2)_n$-[carbohydrate], where n=1–10, including hydrocarbon isomers and hydroxylated derivatives thereof;
    $H_2N$—C(=NH)—NH—NH—$(CH_2)_n$—O-[carbohydrate], where n=1–10, including hydrocarbon isomers, ether linkage isomers and hydroxylated derivatives thereof;
    $H_2N$—C(=NH)—NH—N=CH—$(CH_2)_n$-[carbohydrate], where n 1–10, including hydrocarbon isomers and hydroxylated derivatives thereof;
    $H_2N$—C(=NH)—NH—N=CH—$(CH_2)_n$—O-[carbohydrate], where n 1–10, including hydrocarbon isomers, ether linkage isomers and hydroxylated derivatives thereof.

d. Aminated Sucrose Polyesters. Mixtures of fatty acid hexa-, hepta- and octaesters of sucrose, known as sucrose polyesters, are not hydrolyzed by pancreatic lipase enzymes and are not absorbed in the intestine (Jandacek, 1984). The group claimed herein includes primary amine, aminoguanidine and guanidine derivatives of sucrose polyesters having one or more carbonyl trapping functional group per molecule wherein each carbonyl trapping functional group is in the ω-, ω-1 or other isomeric position within the fatty acyl chains, wherein each fatty acyl chain may have from 3 to 26 carbons and from one to 24 hydroxyl groups.

e. Synthetic polysaccharides consisting partly or entirely of aminosugars bound by β-1,2, β-1,3, β-1,4 and/or β-1,6 linkages.

f. Mixed polysaccharide polymeric derivatives wherin primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and/or aminoalkylbenzene (one to ten carbons per alkyl group) functional groups are covalently attached to matrices such as epichlorohydrin copolymers of cellulose or chitin and wherein hydrocarbon spacer groups may include alkene as well as alkyl groups.

g. Non-polysaccharide polymeric derivatives wherein primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and/or aminoalkylbenzene (one to ten carbons per alkyl group) functional groups are covalently attached to any one of a wide variety of synthetic non-digestible polymers including polystyrene, styrene-divinylbenzene copolymer, polyvinyl alcohol and crosslinked derivatives thereof, and wherein hydrocarbon spacer groups may include alkene as well as alkyl groups.

(v) Administration of Anti-Oxidant and Free Radical Trapping Compound Co-Agents

As regards the use of anti-oxidant and free radical trapping compound co-agents, these substances also can be administered orally. This invention is limited to compositions intended solely for oral used that include at least one primary agent as defined above in section (ii) in combination with one or more anti-oxidant and free radical trapping compound co-agents, co-agents having indirect anti-oxidant activity, vitamin co-agents,-co-agents which facilitate kildney drug elimination, co-agents which are metabolites at risk of depletion, sulfhydryl compound co-agents, co-agents which facilitate glutathione activity, or non-digestible polyamine co-agents, and use thereof via administration by the oral route.

For purposes of the present disclosure, anti-oxidant and free radical trapping compound co-agents are defined as consisting of the following group. It is well established in the prior art that such substances act in vivo as inhibitors of lipid peroxidation.

The therapeutic value of the primary agents of the instant disclosure can be maximized by administration in conjunction with recognized anti-oxidant free radical trapping compounds such as α-tocopherol (Ferrari and coworkers, 1991, pg. 97S; Stuckey, B N, 1968, pp. 214–215), dosage range from 50 I. U. daily to 3,500 I. U. daily or other agents previously recognized as adjunts which facilitate in vivo capability to inhibit lipid peroxidation. The dosage range noted above for α-tocopherol is also claimed for other vitamin E derivatives such as β-tocopherol, γ-tocopherol, δ-tocopherol, ε-tocopherol, $\zeta_1$-tocopherol, $\zeta_2$-tocopherol and η-tocopherol, as well as pharmaceutically acceptable ester derivatives thereof such as the corresponding acetate, succinate and nicotinate forms.

Citric acid, dosage range from 200 mg daily to 20 gm daily, is included in this catagory of co-administered agents, as it is recognized as having anti-oxidant properties (Merck Index, Budavari, S, 1989, pg. 363). Alternatively, this co-agent may be consumed as a combination of potassium citrate monohydrate and citric acid monohydrate in a weight ratio of 3.3 to 1, or other weight ratio selected so as to alkalinize a composition. Citric acid is also recognized as an inhibitor of Maillard reactions (Stuckey, B N, 1968, pg. 210).

In a published list of agents which function to supplement the chain-breaking anti-oxidant property of vitamin E, Tappel (1970, pg. 1138) mentioned ubiquinol and cysteine. A dosage range for cysteine from 100 mg daily to 2 grams daily is proposed herein. A dosage range from 10 mg daily to 500 mg daily for the class of ubiquinols, coenzyme $Q_n$ where n=1–12, is proposed herein. Other substances in this general group include butylated hydroxytoluene (Frankel, E N, 1987, pg. 81), dosage range from 10 mg daily to 1 gm daily; butylated hydroxyanisole (Sies, 1991, pg. 32S), dosage range from 5mg daily to 40 mg daily; propyl gallate (Verhagen and coworkers, 1991, pg. 113), dosage range from 10 mg daily to 1 gm daily; dodecylgallate (Verhagen and coworkers, 1991, pg. 113), dosage range from 10 mg daily to 1 gm daily; tert-butylhydroquinone (Verhagen and coworkers, 1991, pg. 113), dosage range from 10 mg daily to 1 gm daily; β-carotene, dosage range from 10 mg daily to 300 mg daily (Frankel, E N, 1987, pg. 82); dihydrolipoic acid (Sies, 1991, pgs. 33S and 36S), dosage range from 10 mg daily to 500 mg daily; N-acetylcysteine (Le Guen and coworkers, 1992), dosage range from 10 mg/kg daily to 150 mg/kg daily; prostaglandin $B_1$, oligomers (also known as polymeric 15-keto prostaglandin B or $PGB_x$), dosage range from 5 mg/kg daily to 400 mg/kg daily; 2-aminomethyl-4-tert-butyl-6-iodophenol dosage range from 0.5 mg/kg daily to 600 mg/kg daily (Swingle and coworkers, 1985, pg. 120); 2-aminomethyl-4-tert-butyl-6-propionylphenol, dosage range; from 20 mg/kg daily to 500 mg/kg daily (Swingle and coworkers, 1985, pgs. 120–121); 2,6-di-tert-butyl-4-[2'-thenoyl]phenol, dosage range from 3 mg/kg daily to 300 mg/kg daily (Swingle and coworkers, 1985, pg. 121); N,N'-diphenyl-p-phenylenediamine, dosage range from 5 mg/kg daily to 500 mg/kg daily (Swingle and coworkers, 1985, pg. 118); ethoxyquin, dosage range from 5 mg/kg daily to 500 mg/kg daily (Swingle and coworkers, 1985, pg. 118); and probucol, a synthetic anti-oxidant (Halliwell, 1991, pg. 586), dosage range from 25 mg daily to 1 gm daily. Selenium is also included in this group, dosage range from 25 pg daily to 0.5 mg daily, as it has recognized indirect anti-oxidant properties (Stuckey, B N, 1968, pg. 236). Some in vivo experimental data has been presented which indicates that α-tocopherol, butylated-hydroxytoluene, propyl gallate, 2-aminomethyl-4-tert-butyl-6-iodophenol, 2-aminomethyl-4-tert-butyl-6-propionylphenol, 2,6-di-tert-butyl-4-[2'-thenoyl]phenol, N,N'-diphenyl-p-phenylenediamine and ethoxyquin possess both anti-inflammatory and anti-oxidant properties (Schmidt and Bayer, 1990, pg. 149; Honkanen and coworkers, 1990, pg. 190; Swingle and coworkers, 1985, pgs. 114, and 118–121).

Additional anti-oxidants and free radical trapping substances have been recognized as plant (e.g., vegetable) active ingredients. This category, also claimed herein, includes parthenolide, dosage range from 10 mg daily to 1 gm daily; lycopene, dosage range from 10 mg daily to 1 gm daily; daidzin, dosage range from 10 mg daily to 1 gm daily; genistein, dosage range from 10 mg daily to 1 gm daily; quercetin, dosage range from 10 mg daily to 1 gm daily; morin, dosage range from 10 mg daily to 1 gm daily; curcumin, dosage range from 10 mg daily to 1 gm daily; apigenin, dosage range from 10 mg daily to 1 gm daily; sesamol, dosage range from 10 mg daily to 1 gm daily; chlorogenic acid, dosage range from 10 mg daily to 1 gm daily; fisetin, dosage range from 10 mg daily to 1 gm daily; ellagic acid, dosage range from 10 mg daily to 1 gm daily; quillaia saponin dosage range from 10 mg daily to 1 gm daily; capsaicin, dosage range from 10 mg daily to 1 gm daily; ginsenoside, dosage range from 10 mg daily to 1 gm daily; silymarin, dosage range from 10 mg daily to 1 gm daily; kaempferol, dosage range, from 10 mg daily to 1 gm daily; ginkgetin, dosage range from 10 mg daily to 1 gm daily; bilobetin, dosage range from 10 mg daily to 1 gm daily; isoginkgetin, dosage range from 10 mg daily to 1 gm daily; isorhamnetin, dosage range from 10 mg daily to 1 gm daily; herbimycin, dosage range from 10 mg daily to 1 gm daily; rutin, dosage range from 10 mg daily to 1 gm daily; bromelain, dosage range from 10 mg daily to 1 gm daily; levendustin A, dosage range from 10 mg daily to 1 gm daily; and erbstatin, dosage range from 10 mg daily to 1 gm daily.

For the purposes of this invention, dimethyl sulfoxide is exempted from inclusion in this category of co-agent or any other category of co-agent herein.

(vi) Co-Agents Having Indirect Anti-Oxidant Activity

Substances in this category include selenium (10 μg–100 μg daily) and seleno-amino acids having a corresponding molar range of daily use.

(vii) Prophylactic Vitamin Co-Agent Administration

It is another object of this invention that the safety and effectiveness of the products described herein may be optimized by co-administration with the at least one primary agent by the oral route of vitamins which may be inadvertently depleted by the treatment or which may otherwise contribute to the clinical effectiveness of the compositions. For purposes of the present disclosure, vitamin co-agents are defined as consisting of the following group.

retinol, dosage range from 10 μg/kg daily to 1 mg/kg daily;.

vitamin A aldehyde (retinal), dosage range from 10 μg/kg daily to 1 mg/kg daily;

vitamin A acid (retinoic acid), dosage range from 10 μg/kg daily to 1 mg/kg daily;

retinyl acetate, dosage range from 10 ug/kg daily to 1 mg/kg daily;

vitamin $B_1$ (thiamine HCl), dosage range from 1 mg daily to 1.5 gm daily;

thiamine propyl disulfide, dosage range from 1 mg daily to 1.5 gm daily;

vitamin $B_2$ (riboflavin), dosage range from 1 mg daily to 1 gm daily;

riboflavin tetrabutyrate, dosage range from 1 mg daily to 1 gm daily;

riboflavine 5'-phosphate ester monosodium salt, dosage range from 1 mg daily to 1 gm daily;

vitamin $B_6$ (pyridoxine HCl), dosage range from 10 mg daily to 1.75 gm daily;

pyridoxal, dosage range from 1mg daily to 1.75 gm daily;

pyridoxal HCl, dosage range from 10 mg daily to 1.75 gm daily;

pyridoxal 5-phosphate, dosage range from 10 mg daily to 1.75 gm daily;

pyridoxal 5-phosphate calcium salt, dosage range from 10 mg daily to 1.75 gm daily;

pyridoxamine, dosage range from 10 mg daily to 1.75 gm daily;

pyridoxamine dihydrochloride, dosage range from 10 mg daily to 1.75 gm daily;

pyridoxamine phosphate, dosage range from 10 mg daily to 1.75 gm daily;

vitamin $B_{12}$ (cyanocobalamin), dosage range from 1 μg daily to 1 mg daily;

methyl vitamin $B_{12}$ (co-methylcobalamin), dosage range from 1 μg daily to 1 mg daily;

vitamin $D_2$, dosage range from 400 units daily to 40,000 units daily;

vitamin $D_3$, dosage range from 400 units daily to 40,000 units daily;

vitamin $D_4$, dosage range from 400 units daily to 40,000 units daily;

vitamin H (biotin), dosage range from 150 μg daily to 200 mg daily;

vitamin $K_1$ (phytonadione), dosage range from 100 μg daily to 100 mg daily;

diacetyl dihydro vitamin $K_1$, dosage range from 100 μg daily to 100 mg daily;

vitamin $K_1$ oxide, dosage range from 100 μg daily to 100 mg daily;

vitamin(s) $K_2$ (menaquinones), dosage range from 100 μg daily to 100 mg;

vitamin $K_{2(35)}$, dosage range from 100 μg daily 100 mg daily;

vitamin $K_{2(35)}$ dihydrodiacetate, dosage range from 100 μg daily to 100 mg daily;

vitamin $K_{2(30)}$, dosage range from 100 μg daily to 100 mg daily;

vitamin $K_{2(30)}$ dihydrodiacetate, dosage range from 100 μg daily to 100 mg daily;

vitamin $K_5$, range from 100 μg daily to 100 mg daily;

vitamin $K_5$ hydrochloride, dosage range from 100 μg daily to 100 mg daily;

N-acetyl vitamin $K_5$, dosage range from 100 μg daily to 100 mg daily;

vitamin $K_6$, dosage range from 100 μg daily to 100 mg daily;

vitamin $K_6$ dihydrochloride, dosage range from 100 μg daily to 100 mg daily;

vitamin $K_7$, dosage range from 100 μg daily to 100 mg daily;

vitamin $K_7$ hydrochloride, dosage range from 100 μg daily to 100 mg daily;

vitamin K-S(II), dosage range from 100 μg daily to 100 mg daily;

vitamin $L_1$, dosage range from 10 mg daily to 500 mg daily;

vitamin $L_2$, dosage range from 10 mg daily to 500 mg daily;

vitamin U, dosage range from 25 mg daily to 1 gm daily;

methylmethioninesulfonium bromide (bromide analog of vitamin U, dosage range from 25 mg daily to 1 gm daily;

α-carotene, dosage range from 5 mg daily to 200 mg daily;

β-carotene, dosage range from 5 mg daily to 200 mg daily;

γ-carotene, dosage range from 5 mg daily to 200 mg daily;

ω-carotene, dosage range from 5 mg daily to 200 mg daily;

ψ-,ψ-carotene (also known as lycopene; Sies, 1991, pg. 33S), dosage range from 2 mg daily to 200 mg daily;

7,7',8,8',11,12-hexahydro-ψ-,ψ-carotene (also known as phytofluene; Halliwell, 1991, pg. 576), dosage range from 2 mg daily to 200 mg daily;.

L-carnitine (vitamin $B_t$), dosage range from 100 mg daily to 3 gm daily;

acetyl-L-carnitine, dosage range from 100 mg daily to 3 gm daily;

folic acid (vitamin Bc), dosage range from 0.5 mg daily to 50 mg daily;

folinic acid, dosage range from 0.5 mg daily to 50 mg daily;

folinic acid calcium salt pentahydrate, dosage range from 0.5 mg daily to 50 mg daily;

niacinamide, dosage range from 100 mg daily to 10 gm daily;

nicotinic acid (vitamin $B_3$), dosage range from 100 mg daily to 10 gm daily;

nicotinic acid sodium salt sesquihydrate, dosage range from 100 mg daily to 10 gm daily;

nicotinic acid monoethanolamine salt, dosage range from 100 mg daily to 10 gm daily;

pantothenic acid, dosage range from 5 mg daily to 2 gm daily;

pantothenic acid sodium salt, dosage range from 5 mg daily to 2 gm daily; and pantothenic acid calcium salt, dosage range from 5 mg daily to 2 gm daily.

Several of these vitamins possess carbonyl functional groups and thus may be depleted by clinical use of the present invention. Others have a reported anti-oxidant effect, such as the carotenes, or may possess an anti-inflammatory effect, such as carnitine (Elliott and coworkers, 1991), retinoic acid (Fumarulo and coworkers, 1991) and retinyl acetate (Fumarulo and coworkers, 1991).

(viii) Administration of Co-Agents that are Chemical Conjugating Substances Which Facilitate Kidney Drug Elimination For purposes of the present disclosure, co-agents that are metabolites at risk of depletion are defined as consisting of the following group. As regards the use of co-agents which are metabolites at risk of depletion, these substances can be administered orally. It is an object of this invention that the safety and effectiveness of the products described herein may be optimized by co-administration of other metabolites, such as glycine or pharmaceutically acceptable derivatives thereof, which may be depleted within the body during long term drug use. Use of glycine within the dosage range of from 1 gm daily to 20 gm daily is claimed herein. As many of the absorbable amine drugs described herein are excreted from the body as glycine conjugates, co-administration of glycine may be advisable.

(ix) Administration of Co-Agents that are Metabolites at Risk of Depletion

Coenzyme A is a required cofactor for hippuricase, the liver enzyme which adds glycine to benzoic acid derivatives. Activity of hippuricase in glycinating some of the absorbable carbonyl-trapping drugs described herein may sequester a disproportionate fraction of the endogenous coenzyme A pool. Hence co-administration of pantothenic acid, a metabolic precursor of coenzyme A, may also serve to optimize the therapeutic procedures described herein. A dosage range of from 5 mg daily to 2 gm daily for pantothenic acid is claimed herein.

(x) Administration of Sulfhydryl Compound Co-Agents

For purposes of the present disclosure, the category of sulfhydryl compound co-agents is defined as consisting of the following group. As regards the use of sulfhydryl compound co-agents, these substances can be administered orally. Noting the well documented ability of carbonyl agents to react with sulfhydryl groups (Jellum, E et al., 1973), it is an object of this invention to optionally administer sulfhydryl co-agents such as L-methionine, dosage range from 200 mg daily to 4 gm daily and homocysteine, dosage range from 200 mg daily to 2 gm daily. Like the primary agents of the present disclosure, these co-agents may also be of clinical benefit as absorbable drugs capable of covalently binding aldehyde or ketone agents. Homocysteine contains a free sulfhydryl group. Likewise, acetylhomocysteine thiolactone, dosage range from 0.5 mg/kg daily to 25 mg/kg daily is also included in this group. L-Methionine is converted in vivo to homocysteine by several enzymatic reactions which remove a methyl group. L-Methionine also has a demonstrated ability to scavenge hypochlorous acid, a reactive oxygen specie which may contribute to the degradation of hyaluronic acid seen in rheumatoid arthritis (Saari and coworkers, 1993, pgs. 404 and 408). Thioctic acid, also known as $\alpha$-lipoic acid, is also included in this category in a dosage range from 10 mg daily to 500 mg daily, including its sodium salt and ethylenediamine derivatives, as its structure includes a disulfide group. This agent, a recognized growth factor (Merck Index, Budavari, S, 1989, pg. 1469), may tend to be depleted in the tissues of patients having chronic inflammatory diseases involving etiologies which include dysfunction of aldehyde and/or ketone metabolism. The ability of acetaldehyde to combine with thioctic acid, thus deactivating it, has been reported (Smith, W T, 1976, pg. 195).

(xi) Administration of Co-Agent Compounds that Facilitate Glutathione Activity

For purposes of the present disclosure, co-agent compounds that facilitate glutathione activity are defined as consisting of the following group. As regards the use of co-agent compounds that facilitate glutathione activity, these substances can be administered orally. Use of N-acetylcysteine (Dansette and coworkers, 1990), dosage range from 10 mg/kg daily to 150 mg/kg daily, has been reported to increase the levels of plasma cysteine, plasma glutathione and red blood cell glutathione (Bernard, 1991), and to induce a 100-fold increase in myocardial glutathione subsequent to experimental ischemia and reperfusion (Ferrari and coworkers, 1991). N-Acetylcysteine reacts with hypochlorous acid, $HO^-$ and $H_2O_2$ (Bernard, 1991), as well as with reactive aldehydes found in tobacco smoke (Ohman and coworkers, 1992). Other substances in this class of co-agent include L-2-oxothiazolidine-4-carboxylic acid, reported to hydrolyse in vivo to cysteine (Halliwell, 1991, pg. 590), dosage range from 0.3 mmol/kg daily to 3 mmol/kg daily; timonacic, also known as 4-thiazolidinecarboxylic acid (Dansette and coworkers, 1990), dosage range from 10 mg daily to 500 mg daily; cysteamine (Dansette and coworkers, 1990), dosage range from 200 mg daily to 4 gm daily; lipoamide derivatives (Dansette and coworkers, 1990) such as malotilate (Kantec), dosage range from 100 mg daily to 2 gm daily; sulfarlem (ADT; Dansette and coworkers, 1990), dosage range from 100 mg/kg daily to 1 gm/kg daily; and oltipraz (Dansette and coworkers, 1990), dosage range from 100 mg/kg daily to 1 gm/kg daily, as these co-agents can further serve to improve the invention. Glutathione is also included in this category, for daily use in the range of from 10 mg/kg to 150 mg/kg.

(xii) Factors Affecting Daily Dosage Schedule

A daily protocol administered entirely via the oral route of at least one primary agent, in combination with at least one co-agent as defined herein, may be defined such that drug products are administered in timed-release and/or color coded tablets or capsules, so as to facilitate patient compliance and maximize therapeutic value. The primary agent is used in an amount of from about 15 mg/kg/day to about 450 mg/kg/day, more preferably from about 20 mg/kg/day to about 450 mg/kg/day, and most preferably from about 40 mg/kg/day to about 450 mg/kg/day. The co-agent is generally employed in that amount at which is effective, within dosage ranges presented above. Patient dosage schedule compliance may be encouraged by incorporation of the therapeutic composition into a comestible product such as a wafer, cookie or other food carrier.

THERAPEUTIC UTILIZATION

The following examples may serve to illustrate the practical application of this invention. Example One and Example Two are intended for comparison to one another.

EXAMPLE ONE

Pearson and Shaw (1982, pg. 299) described the following summary of an arthritis patient taking vitamin E and vitamin A:

The correct dose of antioxidants for effective arthritis therapy must be determined by experimentation. The effective dose may be quite high. For example, a friend of ours who is a well-known artist in his fifties developed arthritis in his hands. This man's hands became so painful and stiff he could no longer use his fingers to remove the caps from his tubes of paint. He tried vitamin E at increasing dose levels. It was not until he got up to 10,000 I.U. of E and 20,000 I.U. of A per day that he obtained relief from the pain and crippling stiffness. His hands are now flexible and can be used to draw without difficulty. But they remain so only as long as our friend takes 10,000 I.U. of E and 20,000 I.U. of A a day, not less (he's tried).

This dosage of vitamin E far exceeds presently disclosed levels of daily usage, which is in the range from 100 I. U. daily to 3,500 I. U. daily. This particular prior art combination of vitamins E and A, both lipophilic, would not be expected to inhibit any of the free radical reactions taking place in aqueous microenvironments. Nor would it chemically bind and thus deactivate any reactive aldehydes generated by the inflammatory process, as such aldehydes are water soluble.

EXAMPLE TWO

Patient L. S. has a history of arthritis dating back to a serious automobile accident in 1980. By January of 1991 she had serious arthritic involvement of the lumbar spine and chronic hip and knee joint pain on a continuous basis. She had difficulty raising herself from a chair, required the assistance of a cane for activities as simple as walking from her front door to her car, was no longer able to go up or down a flight of stairs, and required use of a prescription analgesic drug every two hours during the night to sleep. She had participated in a program at the Pain Clinic of the University of Miami Medical School and at doctor's advice had used prescription drugs which included Clinoril (R) and Anaprox (R), both non-steroidal anti-inflammatory agents. At the recommendation of this inventor, patient L. S. began taking 800 I.U. dl-α-tocopheryl acetate, 1. g of L-methionine and 1.1 g PABA per day for two months, all three of these substances being consumed entirely via the oral route. Subsequently, the oral administration of dl-α-tocopheryl acetate and L-methionine remained the same and the oral administration of PABA was increased to 2.2 g per day, with the protocol continued on an indefinite basis.

When previously examined by an orthopedics physician a diagnosis was established which included:

. . . Lumbar spine X-Rays in AP and lateral views show extensive degenerative arthritic changes at multiple levels of the lumbar spine . . . severe arthritic changes lumbar spine. Bursitis left greater trochanter clinically . . . She will always have a problem related to her underlying degenerative disease involving her lower back . . . She is favoring her left leg . . . Her straight leg raising is limited on the left side . . .

Ten weeks after initiating this inventor's orally administered PABA/methionine/dl-α-tocopheryl acetate protocol, patient L. S. reported that her arthritis-related pain was much decreased and her functional status much improved. By four months into use of this orally administered therapeutic protocol, patient L. S. had stopped using her cane, had a walking gait that was much improved, had taken to raking leaves in the yard as a form of exercise, and no longer required nighttime analgesics to sleep. At twelve months on this orally administered protocol, patient L. S. reported climbing and descending a flight of stairs without difficulty, and her ability to climb stairs has continued to improve. When re-examined by her orthopedics physician seven months after beginning therapy, who was not informed of her oral use of the PABA/methionine/dl-α-tocopheryl acetate protocol, the doctor noted, in part:

This patient is markedly better. She has normal straight leg raising. She has no significant leg pain. She walks well on her toes and walks well on her heels now without any evidence of motor weakness. There is no limp present.

Unaware of the patient's collaborative effort with this inventor, the orthopedics physician was unable to provide an explanation of the marked improvement in the clinical status of patient L. S. At her office visit patient L. S. noted that she had stopped taking Anaprox, which her orthopedics physician had prescribed seven months earlier.

This inventor recognizes the novel and original composition of primary amine benzoic acid derivatives as primary agents to be orally used with likewise orally administered clinically effective anti-oxidant free radical trapping or inhibiting co-agents as a type of composition likely to have increased beneficial properties for the treatment of chronic inflammatory diseases. This orally administered inventive strategy for the clinical treatment of these diseases has not been previously recognized.

EXAMPLE THREE

A specific composition of carbonyl trapping agent and two co-agents, for use via the oral route from one to five times per day is the following:

| Ingredient | Amount |
| --- | --- |
| PABA | 1.0 gram |
| dl-α-tocopheryl acetate | 400 IU |
| β-carotene | 10 mg |

EXAMPLE FOUR

A specific composition of carbonyl trapping agent and one co-agent, for use via the oral route from one to five times per day is the following:

| Ingredient | Amount |
| --- | --- |
| PABA, potassium salt | 2.0 gram |
| Vitamin E | 800 IU |

EXAMPLE FIVE

A specific composition of carbonyl trapping agent and two co-agents, for use via the oral route from one to five times per day is the following:

| Ingredient | Amount |
| --- | --- |
| PABA | 3.0 grams |
| d-α-tocopheryl succinate | 800 IU |
| chitosan | 1.0 gram |

EXAMPLE SIX

A specific composition of carbonyl trapping agent and one co-agent, for use via the oral route from one to five times per day is the following:

| Ingredient | Amount |
| --- | --- |
| 4-amino-2-hydroxybenzoic acid, potassium salt | 2.0 grams |
| Vitamin E | 800 IU |

EXAMPLE SEVEN

A specific composition of carbonyl trapping agent and two co-agents, for use via the oral route from one to five times per day is the following:

| Ingredient | Amount |
| --- | --- |
| PABA | 2.2 grams |
| Vitamin E | 800 IU |
| Methionine | 1.0 gram |

EXAMPLE EIGHT

A specific composition of carbonyl trapping agent and two co-agents, for use via the oral route from one to five times per day is the following:

| Ingredient | Amount |
| --- | --- |
| 4-(aminomethyl)cyclohexane-carboxylic acid | 1.0 gram |
| butylated hydroxytoluene | 10 mg |
| L-carnitine | 100 mg |

As is true regarding the recognized use of all previously known anti-inflammatory drugs, optimal use of a particular composition of the present invention intended for administration via the oral route must be determined by the physician on a per patient basis.

PABA, many of the other primary agents, as well as many of the co-agents are chemicals which have been previously synthesized and described. Likewise, the general methods of organic synthesis required to make such substances have been described in the prior art. Their methods of manufacture are not contained within the limits of the present disclosure. Yet the present invention recognizes a new and novel combination of primary agent and co-agent therapeutic properties, never recognized previously by people trained in this field, and the orally administered clinical application thereof. This invention constitutes a significant and practical advancement of the clinical therapeutic technology available for treating chronic inflammatory diseases.

Without further elaboration the foregoing will so fully illustrate my invention that others may, by applying current or future knowledge, adapt the same for use under various conditions of service.

REFERENCES CITED

Ahnfelt-Ronne, I et al. "Clinical evidence supporting the radical scavenger mechanism of 5-aminosalicylic acid" *Gastroenterology* 98:1162–1169 (1990)

Austin, P R et al. "Chitin: New facets of research" *Science* 212:749–753 (1981)

Baltes, W "Application of pyrolytic methods in food chemistry" *J. Anal. Appl. Pyrol.* 8:533–545 (1985)

Benedetti, A et al. "Foot-edema induced by carbonyl compounds originating from the peroxidation of liver microsomal lipids" *Biochem. Pharmacol.* 29:121–124 (1980)

Bernard, G R "N-Acetylcysteine in experimental and clinical acute lung injury" *Am. J. Med.* 91(Suppl 3C):54S–59S (1991)

Bingham, S and Cummings, J H "The use of 4-aminobenzoic acid as a marker to validate the completeness of 24 h urine collections in man" *Clin. Sci.* 64:629–635 (1983)

Borne, R F et al. "Anti-inflammatory activity of para-substituted N-benzenesulfonyl derivatives of anthranilic acid" *J. Pharm. Sci.* 63:615–617 (1974)

Budavari, S, ed. *Merck Index*, 11th ed., (Rahway, N.J., Merck & Co., 1989), pages.316, 342, 363, 387, 1469, THER-15 to THER-16

Calabrese, V et al. "Changes in cerebrospinal fluid levels of malondialdehyde and glutathione reductase activity in multiple sclerosis" *Int. J. Clin. Pharm. Res.* 14:119–123 (1994)

Carden, M J et al. "2,5-Hexanedione neuropathy is associated with the covalent crosslinking of neurofilament proteins" *Neurochem. Pathol.* 5:25–35 (1986)

Chio, K S and Tappel, A L "Synthesis and characterization of the fluorescent products derived from malonaldehyde and amino acids" *Biochemistry* 8:2821–2827 (1969)

Chojkier, M et al. "Stimulation of collagen gene expression by ascorbic acid in cultured human fibroblasts" *J. Biol. Chem.* 264:16957–16962 (1989)

Curzio, M et al. "Chemotactic activity of the lipid peroxidation product 4-hydroxynonenal and homologous hydroxyalkenals" *Biol. Chem. Hoppe-Seyler* 367:321–329 (1986)

Curzio, M et al. "Binding of the lipid peroxidation product 4-hydroxynonenlal to human polymorphonuclear leukocytes" *Cell Biochem. Funct.* 12:57–62 (1994)

Dansette, P M et al. "Sulfur containing compounds as antioxidants" in *Antioxidants in TheraPy and Preventive Medicine,* Emerit, I sr. ed. (New York, Plenum Press, 1990) pgs. 209–215

Del Maestro, R F "An approach to free radicals in medicine and biology" *Acta Physiol. Scand.* Suppl. 492:153–168 (1980)

Demopoulos, H B "Control of free radicals in biologic systems" *Fed. Proc.* 32(8):1903–1908 (1973)

Demopoulos, H B et al. "The free radical pathology and the microcirculation in the major central nervous system disorders." *Acta Physiol. Scand.* Suppl. 492:91–119 (1980)

Dowling E J et al. "The ex vivo measurement of malondialdehyde and chemiluminescence as possible indices for anti-inflammatory drug evaluation" *Int. J. Tissue React.* 9:385–391 (1987)

Draper, H H et al. "The metabolism of malondialdehyde" *Lipids* 21:305–307 (1986)

*Drug Information for the Health Care Professional*, 8th ed. (Rockville, Md., United States Pharmacopeial Convention, 1988) pgs. 111–113

Dunlop, A P and Peters, F N *The Furans* (New York, Reinhold Publishing, 1953), pages 280, 308, 353, 371, 373 and 403

Elliot, G R et al. "Acute administration of carnitine to rats modified the basal and A23187-stimulated release of eicosanoids from 4 day carrageenin-elicited peritoneal macrophages" *Agents Actions* 32:88–89 (1991)

Esterbauer, H et al. "Separation and characterization of the aldehydic products of lipid peroxidation stimulated by ADP-$Fe^{2+}$ in rat liver microsomes" *Biochem. J.* 208:129–140 (1982)

Fantone, J C and Ward, P A "Role of oxygen-derived free radicals and metabolites in leukocyte-dependent inflammatory reactions" *Am. J. Pathol.* 107:397–418 (1982)

Feeney, R E et al. "Carbonyl-amine reactions in protein chemistry" *Adv. Protein Chem.* 29:135–203 (1975), pages 136, 137, 141 and 144 Ferrari, R et al. "Oxygen free radicals and myocardial damage: Protective role of thiol-containing agents" *Am. J. Med.* 91(Suppl 3C):95S–105S (1991)

Frankel, E N "Secondary products of lipid oxidation" *Chem. Phys. Lipids* 44:73–85 (1987)

Fumarulo, R et al. "Retinoids inhibit the respiratory burst and degranulation of stimulated human polymorphonuclear leukocytes" *Agents Actions* 34:339–344 (1991)

Gougerot, M M and Hewitt, J ["Scleroderma in patches, combined action of para-aminobenzoic acid and of alpha-tocopherol"] *Bull. Soc. Fr. Dermatol. Syph.* 58:42–43 (1951)

Grootveld, M and Halliwell, B "2,3-Dihydroxybenzoic acid is a product of human aspirin metabolism" *Biochem. Pharmacol.* 37:271–280 (1988)

Gross, V et al. "Free radicals in inflammatory bowel diseases" Pathology and therapeutic implications" *Hepato-Gastroenterol.* 41:320–327 (1994)

Gutteridge, J M and Wilkins, S "Copper-dependent hydroxyl radical damage to ascorbic-acid. Formation of a thiobarbituric acid-reactive product" *FEBS Lett.* 137:327–330 (1982)

Hall, E D "Beneficial effects of the 21-aminosteroid U74006F in acute CNS trauma and hypovolemic shock" *Acta Anaesth. Belg.* 38:421–425 (1987)

Halliwell, B and Gutteridge, J M "The importance of free radicals and catalytic metal ions in human diseases" *Molec. Aspects Med.* 8:89–193 (198)

Halliwell, B "Drug antioxidant effects: A basis for drug selections?" *Drugs* 42:569–605 (1991)

Hatherill, J R et al. "Mechanism of oxidant-induced changes in erythrocytes" *Agents Actions* 32:351–358 (1991)

Higson, F K et al. "Iron enhancement of ascorbate toxicity" *Free Rad. Res. Comms.* 5:107–115 (1988)

Holdren, R F and Hixon, R M "The reaction of 2-methylfuran with formaldehyde and substituted ammonium chlorides" *J. Am. Chem. Soc.* 68:1198–1200(1946)

Honkanen, V E et al. "Serum cholesterol and vitamins A and E in juvenile chronic arthritis" *Clin. Exp. Rheum.* 8:187–191 (1990)

Howie, M B and Bourke, E "Metabolism of p-aminobenzoic acid in the perfused livers of chronically uraemic rats" *Clin. Sci.* 56:9–14 (1979)

Huff, B B, ed., *Physicians' Desk Reference*, 34th ed. (Oradell, N.J., Medical Economics Co., 1980) pgs. 849 and 1430

Hunter, M I et al. "Lipid peroxidation products and antioxidant proteins in plasma and cerebrospinal fluid from multiple sclerosis patients" *Neurochem. Res.* 10:1645–1652 (1985)

Jackson, M J et al. "Techniques for studying free radical damage in muscular dystrophy" *Med. Biol.* 62:135–138 (1984)

Jandacek, R J "Studies with sucrose polyester" *Int. J. Obes.* 8(Suppl 1):13–21 (1984)

Jasin, H E "Oxidative modification of inflammatory synovial fluid immunoglobulin G" *Inflammation* 17:167–181 (1993)

Jellum, E et al. "The presence of furan derivatives in patients receiving fructose-containing solutions intravenously" *Clin. Chim. Acta* 47:191–201 (1973)

Kar, N C and Pearson, C M "Catalase, superoxide dismutase, glutathione reductase and thiobarbituric acid-reactive products in normal and dystrophic human muscle" *Clin. Chim. Acta* 94:277–280 (1979)

Katsnelson, B A et al. "Trends and perspectives of the biological prophylaxis of silicosis" *Environ. Health Perspect.* 82:311–321 (1989)

Kessler, G "Nature's Plus Natural Vitamin Handbook" (Farmingdale, N.Y., Natural Organics, Inc., 1990), page 87

Konecki, J et al. "Histochemical changes in the small intestine in acute furfural poisoning" *Folia Histochem. Cytochem.* 12:59–66 (1974)

Kontos, H A et al. "Prostaglandins in physiological and in certain pathological responses of the cerebral circulation" *Fed. Proc.* 40:2326–2330 (1981)

Kostyuk, V A et al;. ["Antioxidative activity of the antiarthritic drugs"] *Vopr. Med. Khim.* 36(3):37–39 (1990)

Kurdin, A N ["Free radical lipid oxidation in the pathogenesis of myocardial infarction"] *Kardiologia* 18:115–118 (1978)

Kushner, I, ed. *Understanding Arthritis* (New York, Charles Scribner's Sons, 1984), pages 52–53, and 55–57

Le Guen, C A et al. "Captopril inhibits the fluorescence development associated with glycation of proteins" *Agents Actions* 36:264–270 (1992)

Lever, M et al. "Automated fluorimetric determination of furfurals" *Anal. Biochem.* 144:6–14 (1985)

Lukoschek, M et al. "[Synovial membrane and cartilage changes in an arthrosis model. Instability and impact stress model]" *Z. Orthop. Ihre. Grenzgeb.* 128:437–441 (1990)

Maksimov, O B and Rebachuk, N M ["Screening for the presence of antioxidants in plant extracts"] *Rastit. Resur.* 21(2):216–220 (1985)

Mapp, P I et al. "Hypoxia, oxidative stress and rheumatoid arthritis" *Br. Med. Bull.* 51:419–436 (1995)

McKenzie, S J et al. "Evidence of oxidant-induced injury to epithelial cells during inflammatory bowel disease" *J. Clin. Invest.* 98:136–141 (1996)

Muus, P et al. "Plasma levels of malondialdehyde, a product of cyclo-oxygenase-dependent and independent lipid peroxidation, in rheumatoid arthritis: a correlation with disease activity" *Prostaglandins Med.* 2:63–65 (1979)

Nakken, K F "The action of X-rays on dilute solutions of p-aminobenzoic acid" *Radiation Res.* 21:446–461 (1964)

Nakken, K F and Pihl, A "The X-ray-induced damage to the p-aminobenzoic acid moiety of folic acid and some other p-aminobenzoic acid conjugates irradiated in solution" *Radiation Res.* 27:19–31 (1966)

Ohman, L et al. "N-Acetylcysteine enhances receptor-mediated phagocytosis by human neutrophils" *Agents Actions* 36:271–277 (1992)

Olney, J W et al. "L-Cysteine, a bicarbonate-sensitive endogenous excitotoxin" *Science* 248:596–599 (1990)

Ortwerth, B J and Olesen, P R "Ascorbic acid-induced crosslinking of lens proteins: evidence supporting a Maillard reaction" *Biochim. Biophys. Acta* 956:10–22 (1988)

Passwater, R A *The Antioxidants. The Nutrients that Guard the Body Against Cancer, Heart Disease, Arthritis and Allergies—and Even Slow the Aging Process* (New Canaan, Conn., Keats Publishing, 1985)

Pearson, D and Shaw, S *Life Extension. A Practical Scientific Approach* (New York, Warner Books, 1982) pages 298–300, 468–469 and 611–613

Pettersen, J E and Jellum, E "The identification and metabolic origin of 2-furoylglycine and 2,5-furandicarboxylic acid in human urine" *Clin. Chim. Acta* 41:199–207 (1972)

Pitner, M A "Pathophysiology of overuse injuries in the hand and wrist" *Hand Clin.* 6:355–364 (1990)

Priestley, G C and Brown, J C "Effects of potassium para-aminobenzoate on growth and macromolecule synthesis in fibroblasts cultured from normal and sclerodermatous human skin, and rheumatoid synovial cells" *J. Invest. Dermatol.* 72:161–164 (1979)

Pryor, W A et al. "Autoxidation of polyunsaturated fatty acids. Part 1. Effect of ozone on the autoxidation of neat methyl linoleate and methyl linolenate" *Arch. Environ. Health* 31:201–210 (1976)

Pucheu, S et al. "Assessment of radical activity during the acute phase of myocardial infarction following fibrinolysis: utility of assaying plasma malondialdehyde" *Free Radic. Biol. Med.* 19:873–881 (1995)

Repine, J E et al. "Generation of hydroxyl radical by enzymes, chemicals, and human phagocytes in vitro. Detection with the anti-inflammatory agent, dimethyl sulfoxide" *J. Clin. Invest.* 64:1642–1651 (1979)

Rice, E W "Furfural: exogenous precursor of certain urinary furans and possible toxicologic agent in humans" *Clin. Chem.* 18:1550–1551 (1972)

Richmond, R et al. "Superoxide-dependent formation of hydroxyl radicals: detection of hydroxyl radicals by the hydroxylation of aromatic compounds" *Anal. Biochem.* 118:328–335 (1981)

Rossi, M A et al. "Effect of 4-hydroxy-2,3-trans-nonenal and related aldehydes on phospholipase C activity of rat neutrophils" *Int. J. Tissue React.* 15:201–205 (1993)

Rowley, D et al. "Lipid peroxidation in rheumatoid arthritis: thiobarbituric acid-reactive material and catalytic iron salts in synovial fluid from rheumatoid patients" *Clin. Sci.* 66:691–695 (1984)

Saari, H et al. "Differential effects of reactive oxygen species on native synovial fluid and purified human umbilical cord hyaluronate" *Inflammation* 17:403–415 (1993)

Sawicki, E et al. "Comparison of spectrophotometric and spectrophotofluorometric methods for the determination of malonaldehyde" *Anal. Chem.* 35:199–205 (1963)

Schauenstein, E and Esterbauer, H *Aldehydes in Biological Systems. Their Natural Occurrence and Biological Activities* (London, Pion Limited, 1977) pages. 181–194

Schmidt, K H and Bayer, W "Efficacy of vitamin E as a drug in inflammatory joint diseases" in *Antioxidants in Therapy and Preventive Medicine,* Emerit, I, sr. ed. (New York, Plenum Press, 1990) pgs. 147–150

Scott, C C and Robbins, E B "Toxicity of p-aminobenzoic acid" *Proc. Soc. Exp. Biol. Med.* 49:184–186 (1942)

Scott, G "Antioxidants: Radical chain-breaking mechanisms" in *Atmospheric Oxidation and Antioxidants* (New York, Elsevier Publishing Co., 1965) pages 120, 125, 127, 145, 148 and 158

Selley, M L et al. "Occurrence of (E)-4-hydroxy-2-nonenal in plasma and synovial fluid of patients with rheumatoid arthritis and osteosrthritis" *Ann. Rheum. Dis.* 51:481–484 (1992).

Sestili M A "Possible adverse health effects of vitamin C and ascorbic acid" *Semin Oncol* 10:299–304 (1983)

Shimizu, J and Watanabe, M "Gas chromatographic analysis of furfural and hydroxymethyl-furfural in wine" *Agric. Biol. Chem.* 43:1365–1366 (1979)

Sies, H "Oxidative stress: From basic research to clinical application" *Am. J. Med.* 91(Suppl 3C);31S–38S (1991)

Sigma Chemical Co. catalog, Feb. 1994 (Saint Louis)

Slight, S H et al. "Glycation of lens proteins by the oxidation products of ascorbic acid" *Biochim. Biophys. Acta* 1038:367–374 (1990)

Smith, W T "Nutritional deficiencies and disorders" in *Greenfield's Neurology,* Blackwood, W and Corsellis, JAN, eds. (Chicago, Year Book Medical Publishers, 1976) pp. 194–237

Stuckey, B N "Antioxidants as food stabilizers" in *CRC Handbook of Food Additives,* Furia, T E, ed. (West Palm Beach, Fla., CRC Press, 1968) pages 210, 214–215, and 236

Swingle, K F et al. "Anti-inflammatory activity of antioxidants" in *Anti-Inflammatory and Anti-Rheumatic Drugs. Vol. III: Anti-Rheumatic Drugs, Experimental Agents, and Clinical Aspects of Drug Use,* Rainsford, K D, ed. (Boca Raton, Fla., CRC Press, 1985) pgs.105–126

Tamai, H et al. "Induction of colitis in rats by 2,2'-azobis (amidinopropane) dihydrochloride" *Inflammation* 16:69–81 (1992)

Tappel, A L "Biological antioxidant protection against lipid peroxidation damage" *Am. J. Clin. Nutr.* 23:1137–1139 (1970)

Ulbricht, R J et al. "A review of 5-hydroxymethylfurfural (HMF) in parenteral solutions" *Exp. Appl. Toxicol.* 4:843–853 (1984)

Verhagen, H et al. "Butylated hydroxyanisole in perspective" *Chem. Biol. Interact.* 80:109–134 (1991)

Weissmann, G "Aspirin" *Scientific American* 264:84–90 (1991)

Weizman, Z et al. "Bentiromide test for assessing pancreatic dysfunction using analysis of para-aminobenzoic acid in plasma and urine" *Gastroenterology* 89:596–604 (1985)

Winitz, M et al. "Studies in metabolic nutrition employing chemically defined diets. I. Extended feeding of normal human adult males" *Am. J. Clin. Nutr.* 23:525–545 (1970)

Winyard, P G et al. "Presence of foam cells containing oxidised low density lipoprotein in the synovial membrane from patients with rheumatoid arthritis" *Ann. Rheumatic Dis.* 52:677–680 (1993)

Wong, S F et al. "The role of superoxide and hydroxyl radicals in the degradation of hyaluronic acid induced by metal ions and by ascorbic acid" *J. Inorg. Biochem.* 14:127–134 (1981)

Yalpani, M *Polysaccharides: Syntheses, Modifications and Structure-Property Relations* (New York, Elsevier, 1988), pages 22, 214, 250, 252, 281, 282, 389 and 390

Young, D S et, al. "Influence of a chemically defined diet on the composition of serum and urine" *Clin. Chem.* 17:765–773 (1971)

Zarafonetis, C D "Clinical use of para-aminobenzoic acid" *Texas State J. Med.* 49:666–672 (1953)

Zarafonetis, C J "Antifibrotic therapy with Potaba" *Am. J. Med. Sci.* 248:550–561 (1964)

Zarafonetis, C J et al. "Retrospective studies in scleroderma: effect of potassium para-aminobenzoate on survival" *J. Clin. Epidemiol.* 41:193–205 (1988)

Zivin, J A and Choi, D W "Stroke therapy" *Sci. Am.* 265:56–63 (1991)

Zuckerman, J E et al. "Evaluation of antifibrotic drugs in bleomycin-induced pulmonary fibrosis in hamsters" *J. Pharmacol. Exp. Ther.* 213:425–431 (1980)

I claim:

1. A method of treating a mammalian subject for the symptoms of a chronic inflammatory disorder, said method comprising daily systemic administration entirely by the oral route to said subject a composition consisting essentially of (a) from about 15 mg/kg to about 450 mg/kg of a water soluble primary amine compound having a molecular weight in the range of 100 to about 1,400 of the formula

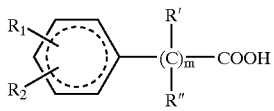

wherein the 6-membered ring is phenyl, cyclohexadiene, cyclohexene or cyclohexane; and wherein $R_1$ is —$NH_2$; aminoalkyl- having 1–10 carbons; —NHC(=NH)$NH_2$; —$(CH_2)_n$NHC(=NH)$NH_2$ wherein n is 1–10; —C(=NH)$NH_2$; —$(CH_2)_n$—CH=NC(=NH)$NH_2$ wherein n is 1–10; —NHC(=NH)$NHNH_2$; —$(CH_2)_n$NHC(=NH)$NHNH_2$ wherein n is 1–10; —$(CH_2)_n$—CH=NC(=NH)$NHNH_2$ wherein n is 1–10; —NHNHC(=NH)$NH_2$; —$(CH_2)_n$—NHNHC(=NH)$NH_2$ wherein n is 1–10; or —$(CH_2)_n$—CH=N—NHC(=NH)$NH_2$ wherein n is 1–10;

$R_2$ is H; —OH; —O—$CH_3$; —O—R wherein R is alkyl of 2–10 carbons; aminoalkyl wherein the alkyl group is 1–10 carbons; —$SO_3H$; —$CH_3$; and —$(CH_2)_nCH_3$ wherein n is 1–10;

R' and R" are —H, OH or $CH_3$; and m is 0 or 1;

and the pharmaceutically acceptable salts, esters, and amide derivatives thereof; and (b) a therapeutically effective amount of at least one co-agent selected from the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity; wherein the amount of the primary agent on a molar basis is always greater than that of a co-agent.

2. A method of treating a mammalian subject for the symptoms of a chronic inflammatory disorder, said method comprising daily systemic administration entirely by the oral route to said subject a composition consisting essentially of (a) from about 15 mg/kg to about 450 mg/kg of a water soluble primary amine compound having a molecular weight in the range of 100 to about 1,400 of the formula

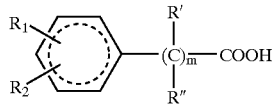

wherein the 6-membered ring is phenyl, cyclohexadiene, cyclohexene or cyclohexane; and wherein $R_1$ is —$NH_2$; aminoalkyl- having 1–10 carbons; —NHC(=NH)$NH_2$; —$(CH_2)_n$NHC(=NH)$NH_2$ wherein n is 1–10; —C(=NH)$NH_2$; —$(CH_2)_n$—CH=NC(=NH)$NH_2$ wherein n is 1–10; —NHC(=NH)$NHNH_2$; —$(CH_2)_n$NHC(=NH)$NHNH_2$ wherein n is 1–10; —$(CH_2)_n$—CH=NC(=NH)$NHNH_2$ wherein n is 1–10; —NHNHC(=NH)$NH_2$; —$(CH_2)_n$—NHNHC(=NH)$NH_2$ wherein n is 1–10; or —$(CH_2)_n$—CH=N—NHC(=NH)$NH_2$ wherein n is 1–10;

$R_2$ is H; —OH; —O—$CH_3$; —O—R wherein R is alkyl of 2–10 carbons; aminoalkyl wherein the alkyl group is 1–10 carbons; —$SO_3H$; —$CH_3$; and —$(CH_2)_nCH_3$ wherein n is 1–10;

R' and R" are —H, OH or $CH_3$; and m is 0 or 1;

and the pharmaceutically acceptable salts, esters, and amide derivatives thereof; and (b) a therapeutically effective amount of at least one co-agent selected from the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity; and (c) a therapeutically effective amount of an additional co-agent that is a non-digestible polyamine;

wherein the amount of the primary agent on a molar basis is always greater than that of a co-agent.

3. The method of claim 2 wherein the non-digestible polyamine of groups a, c or f is a chitin derivative.

4. The method of claim 2 wherein the non-digestible polyamine of group b is a chitosan derivative.

5. The method of claim 2 wherein the non-digestible polyamine of groups c or f is a cellulose derivative.

6. The method of claim 2 wherein said mammalian subject is a human and the therapeutically effective amount of said non-digestible polyamine co-agent is a dosage in the range of from about 15 mg/kg/day to about 450 mg/kg/day.

7. The method of claim 1 wherein said co-agent is selected from the group consisting of a) at least one anti-oxidant and free radical trapping compound selected from the group consisting of α-tocopherol, β-tocopherol, γ-tocopherol, δ-tocopherol, ε-tocopherol, $ζ_1$-tocopherol, $ζ_2$-tocopherol and η-tocopherol, and pharmaceutically acceptable ester derivatives thereof, with the proviso that said tocopherol substances are used for adult human consumption in a dosage no less than 50 I.U. daily; β-carotene; vitamin A; butylated hydroxytoluene; butylated hydroxyanisole; propyl gallate; dodecylgallate; tert-butylhydroquinone; citric acid; cysteine;

ubiquinols; glutathione; dihydrolipoic acid; N-acetylcysteine; prostaglandin $B_1$ oligomers; 2-aminomethyl-4-tert-butyl-6-iodophenol; 2-aminomethyl-4-tert-butyl-6-propionylphenol; 2,6-di-tert-butyl-4-[2'-thenoyl]phenol; N,N'-diphenyl-p-phenylenediamine; ethoxyquin; probucol; parthenolide; lycopene; daidzin; genistein; quercetin; morin; curcumin; apigenin; sesamol; chlorogenic acid; fisetin; ellagic acid; quillaia saponin; capsaicin; ginsenoside; silymarin; kaempferol; ginkgetin; bilobetin; isoginkgetin; isorhamnetin; herbimycin; rutin; bromelain; levendustin A; and erbstatin, b) a compound having indirect anti-oxidant properties selected from the group consisting of selenium and seleno-containing amino acids, c) a vitamin selected from the group consisting of vitamin A; retinal; retinoic acid; retinyl acetate; thiamine; thiamine propyl disulfide; riboflavin; riboflavin tetrabutyrate; riboflavine 5'-phosphate ester monosodium salt; pyridoxine; pyridoxal; pyridoxal HCl; pyridoxal 5-phosphate; pyridoxal 5-phosphate calcium salt; pyridoxamine; pyridoxamine dihydrochloride; pyridoxamine phosphate; cyanocobalamin; co-methylcobalamin; vitamin $D_2$; vitamin $D_3$; vitamin $D_4$; biotin; vitamin $K_1$; vitamin $K_1$ oxide; vitamins of the $K_2$ series; vitamin $K_5$; vitamin $K_5$ hydrochloride; vitamin $K_6$; vitamin $K_6$ dihydrochloride; vitamin $K_7$; vitamin $K_7$ hydrochloride; vitamin K-S(II); vitamin $L_1$; vitamin $L_2$; vitamin U; methylmethioninesulfonium bromide; α-carotene; β-carotene; γ-carotene; ω-carotene; ψ-,ψ-carotene; 7,7',8,8',11,12-hexahydro-ψ-,ψ-carotene; carnitine; acetyl-L-carnitine; folic acid; folinic acid; folinic acid calcium salt pentahydrate; niacinamide; nicotinic acid; nicotinic acid sodium salt sesquihydrate; nicotinic acid monoethanolamine salt; pantothenic acid; pantothenic acid sodium salt; and pantothenic acid calcium salt, d) a chemical conjugating substance which facilitates kidney drug elimination selected from the group consisting of glycine and pharmaceutically acceptable derivatives thereof, e) a metabolite at risk of depletion selected from the group consisting of pantothenic acid and pharmaceutically acceptable derivatives thereof, f) a sulfhydryl compound selected from the group consisting of homocysteine, acetylhomocysteine thiolactone, L-methionine or α-lipoic acid, or g) a chemical which acts to facilitate glutathione activity, selected from the group consisting of N-acetylcysteine, L-2-oxothiazolidine-4-carboxylate, timonacic, cysteamine, malotilate, sulfarlem, oltipraz and glutathione.

8. The method of claim 1 wherein the subject is a veterinary mammal and the at least one co-agent is selected from the group consisting of a) at least one anti-oxidant and free radical trapping compound selected from the group consisting of α-tocopherol, β-tocopherol, γ-tocopherol, δ-tocopherol, ε-tocopherol, $ζ_1$-tocopherol, $ζ_2$-tocopherol and η-tocopherol, and pharmaceutically acceptable ester derivatives thereof, with the proviso that said tocopherol substances are used for veterinary mammal consumption in a dosage comparable on a basis of grams per body weight to adult human dosage of no less than 50 I.U. daily; β-carotene; vitamin A; butylated hydroxytoluene; butylated hydroxyanisole; propyl gallate; dodecylgallate; tert-butylhydroquinone; citric acid; cysteine; ubiquinols; glutathione; dihydrolipoic acid; N-acetylcysteine; prostaglandin $B_1$ oligomers; 2-aminomethyl-4-tert-butyl-6-iodophenol; 2-aminomethyl-4-tert-butyl-6-propionylphenol; 2,6-di-tert-butyl-4-[2'-thenoyl]phenol; N,N'-diphenyl-p-phenylenediamine; ethoxyquin; probucol; parthenolide; lycopene; daidzin; genistein; quercetin; morin; curcumin; apigenin; sesamol; chlorogenic acid; fisetin; ellagic acid; quillaia saponin; capsaicin; ginsenoside; silymarin; kaempferol; ginkgetin; bilobetin; isoginkgetin; isorhamnetin; herbimycin; rutin; bromelain; levendustin A; and erbstatin, b) a compound having indirect anti-oxidant properties selected from the group consisting of selenium and seleno-containing amino acids, c) a vitamin selected from the group consisting of vitamin A; retinal; retinoic acid; retinyl acetate; thiamine; thiamine propyl disulfide; riboflavin; riboflavin tetrabutyrate; riboflavine 5'-phosphate ester monosodium salt; pyridoxine; pyridoxal; pyridoxal HCl; pyridoxal 5-phosphate; pyridoxal 5-phosphate calcium salt; pyridoxamine; pyridoxamine dihydrochloride; pyridoxamine phosphate; cyanocobalamin; co-methylcobalamin; vitamin $D_2$; vitamin $D_3$; vitamin $D_4$; biotin; vitamin $K_1$; vitamin $K_1$ oxide; vitamins of the $K_2$ series; vitamin $K_5$; vitamin $K_5$ hydrochloride; vitamin $K_6$; vitamin $K_6$ dihydrochloride; vitamin $K_7$; vitamin $K_7$ hydrochloride; vitamin K-S(II); vitamin $L_1$; vitamin $L_2$; vitamin U; methylmethioninesulfonium bromide; α-carotene; β-carotene; γ-carotene; ω-carotene; ψ-,ψ-carotene; 7,7',8,8',11,12-hexahydro-ψ-,ψ-carotene; carnitine; acetyl-L-carnitine; folic acid; folinic acid; folinic acid calcium salt pentahydrate; niacinamide; nicotinic acid; nicotinic acid sodium salt sesquihydrate; nicotinic acid monoethanolamine salt; pantothenic acid; pantothenic acid sodium salt; and pantothenic acid calcium salt, d) a chemical conjugating substance which facilitates kidney drug elimination selected from the group consisting of glycine and pharmaceutically acceptable derivatives thereof, e) a metabolite at risk of depletion selected from the group consisting of pantothenic acid and pharmaceutically acceptable derivatives thereof, f) a sulfhydryl compound selected from the group consisting of homocysteine, acetylhomocysteine thiolactone, methionine or α-lipoic acid, or g) a chemical which acts to facilitate glutathione activity, selected from the group consisting of N-acetylcysteine, L-2-oxothiazolidine-4-carboxylate, timonacic, cysteamine, malotilate, sulfarlem, oltipraz and glutathione.

9. A composition for treating a mammalian subject for symptoms of a chronic inflammatory disorder, said composition consisting essentially of (a) a therapeutically effective amount of a primary agent consisting of a water soluble primary amine compound having a molecular weight in the range of 100 to about 1,400 of the formula

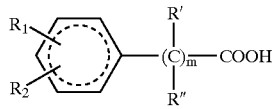

wherein the 6-membered ring is phenyl, cyclohexadiene, cyclohexene or cyclohexane; and wherein R₁ is —NH₂; aminoalkyl- having 1–10 carbons; —NHC(=NH)NH₂; —(CH₂)$_n$NHC(=NH)NH₂ wherein n is 1–10; —C(=NH)NH₂; —(CH₂)$_n$—CH=NC(=NH)NH₂ wherein n is 1–10; —NHC(=NH)NHNH₂; —(CH₂)$_n$NHC(=NH)NHNH2 wherein n is 1–10; —(CH₂)$_n$—CH=NC(=NH)NHNH₂ wherein n is 1–10; —NHNHC(=NH)NH₂; —(CH₂)$_n$—NHNHC(=NH)NH₂ wherein n is 1–10; or —(CH₂)$_n$—CH=N—NHC(=NH)NH₂ wherein n is 1–10;

R₂ is H; —OH; —O—CH₃; —O—R wherein R is alkyl of 2–10 carbons; aminoalkyl wherein the alkyl group is 1–10 carbons; —SO₃H; —CH₃; and —(CH₂)$_n$CH₃ wherein n is 1–10;

R' and R" are —H, OH or CH₃; and m is 0 or 1;

and the pharmaceutically acceptable salts, esters, and amide derivatives thereof; and (b) a therapeutically effective amount of at least one co-agent selected from the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity;

wherein the amount of the primary agent on a molar basis is always greater than that of a co-agent.

10. The composition of claim 9 wherein the co-agent is selected from a compound of claim 7.

11. A composition for treating a mammalian subject for symptoms of a chronic inflammatory disorder, said composition consisting essentially of (a) a therapeutically effective amount of a primary agent consisting of a water soluble primary amine compound having a molecular weight in the range of 100 to about 1,400 of the formula $$R_1 \underset{R_2}{\diagdown}\!\!\!\bigcirc\!\!\!\diagup\!\!-\!(C)_m\!\!\underset{R''}{\overset{R'}{|}}\!\!-COOH$$

wherein the 6-membered ring is phenyl, cyclohexadiene, cyclohexene or cyclohexane; and wherein R₁ is —NH₂; aminoalkyl- having 1–10 carbons; —NHC(=NH)NH₂; —(CH₂)$_n$NHC(=NH)NH₂ wherein n is 1–10; —C(=NH)NH₂; —(CH₂)$_n$—CH=NC(=NH)NH₂ wherein n is 1–10; —NHC(=NH)NHNH₂; —(CH₂)$_n$NHC(=NH)NHNH₂ wherein n is 1–10; —(CH₂)$_n$—CH=NC(=NH)NHNH₂ wherein n is 1–10; —NHNHC(=NH)NH₂; —(CH₂)$_n$—NHNHC(=NH)NH₂ wherein n is 1–10; or —(CH₂)$_n$—CH=N—NHC(=NH)NH₂ wherein n is 1–10;

R₂ is H; —OH; —O—CH₃; —O—R wherein R is alkyl of 2–10 carbons; aminoalkyl wherein the alkyl group is 1–10 carbons; —SO₃H; —CH₃; and —(CH₂)$_n$CH₃ wherein n is 1–10;

R' and R" are —H, OH or CH₃; and m is 0 or 1;

and the pharmaceutically acceptable salts, esters, and amide derivatives thereof; and (b) a therapeutically effective amount of at least one co-agent selected from the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity; and (c) a therapeutically effective amount of an additional co-agent that is a non-digestible polyamine;

wherein the amount of the primary agent on a molar basis is always greater than that of a co-agent.

12. The composition of claim 9 wherein the non-digestible polyamine of groups a, c or f is a chitin derivative.

13. The composition of claim 9 wherein the non-digestible polyamine of group b is a chitosan derivative.

14. The composition of claim 9 wherein the non-digestible polyamine of groups c or f is a cellulose derivative.

15. A composition for treating a mammalian subject for symptoms of a chronic inflammatory disorder, said composition consisting essentially of (a) a therapeutically effective amount of a primary agent consisting of a water soluble primary amine compound having a molecular weight in the range of 100 to about 1,400 of the formula $$R_1 \underset{R_2}{\diagdown}\!\!\!\bigcirc\!\!\!\diagup\!\!-\!(C)_m\!\!\underset{R''}{\overset{R'}{|}}\!\!-COOH$$

wherein the 6-membered ring is phenyl, cyclohexadiene, cyclohexene or cyclohexane; and wherein R₁ is —NH₂; aminoalkyl- having 1–10 carbons; —NHC(=NH)NH₂; —(CH₂)$_n$NHC(=NH)NH₂ wherein n is 1–10; —C(=NH)NH₂; —(CH₂)$_n$—CH=NC(=NH)NH₂ wherein n is 1–10; —NHC(=NH)NHNH₂; —(CH₂)$_n$NHC(=NH)NHNH₂ wherein n is 1–10; —(CH₂)$_n$—CH=NC(=NH)NHNH₂ wherein n is 1–10; —NHNHC(=NH)NH₂; —(CH₂)$_n$—NHNHC(=NH)NH₂ wherein n is 1–10; or —(CH₂)$_n$—CH=N—NHC(=NH)NH₂ wherein n is 1–10;

R₂ is H; —OH; —O—CH₃; —O—R wherein R is alkyl of 2–10 carbons; aminoalkyl wherein the alkyl group is 1–10 carbons; —SO₃H; —CH₃; and —(CH₂)$_n$CH₃ wherein n is 1–10;

R' and R" are —H, OH or CH₃; and m is 0 or 1;

and the pharmaceutically acceptable salts, esters, and amide derivatives thereof; and (b) a therapeutically effective amount of at least one co-agent selected from the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity; and (c) a pharmaceutically acceptable carrier;

wherein the amount of the primary agent on a molar basis is always greater than that of a co-agent.

16. A composition according to claim 15 wherein the pharmaceutically acceptable carrier is an aqueous solution or suspension for oral use, a comestible product for oral use, or a combination thereof.

17. A composition according to claim 16 wherein the comestible product for oral use is a capsule, a sustained-release capsule, a tablet, a sustained-release tablet or a foodstuff.

18. The method of claim 2 wherein the co-agent that is a non-digestible polyamine is selected from the group consisting of a. a naturally occurring polysaccharide having β-1,2, β-1,3, β-1,4 and/or β-1,6 linkages containing aminosugars;

b. a deacetylated, naturally occurring polysaccharide having at least one N-acetylated residue which is a high molecular weight polysaccharide bearing primary amine groups directly linked to sugar carbons;

c. a naturally occurring polysaccharide which has been chemically derivatized selected from the group consisting of
  i) aminodeoxy polysaccharide,
  ii) aminoalkyl, amino(hydroxyalkyl), aminoalkyl-ether, and amino(hydroxyalkyl)-ether derivatives selected from the group consisting of
    a) $H_2N-(CH_2)_n$-polysaccharide,
    b) aminoisoalkylpolysaccharide wherein the alkyl group has 1–10 carbons,
    c) $H_2N-(CH_2)_n-CHOH-(CH_2)_n$-polysaccharide wherein m and n are each 0–10,
    d) $H_2N-(CH_2)_n-O$-polysaccharide, and
    e) $H_2N-(CH_2)_n-CHOH-(CH_2)_n-O$-polysaccharide wherein m and n are each 0–10,
  iii) aminobenzyl and aminoalkylbenzyl derivatives selected from the group consisting of
    a) $H_2N-C_6H_4-(CH_2)_n$-polysaccharide wherein n=0–10
    b) $H_2N-CH_2-C_6H_4-(CH_2)_n$-polysaccharide wherein n=0–10
    c) $H_2N-C_6H_4-(CH_2)_n-O$-polysaccharide wherein n=0–10 and
    d) $H_2N-C_6H_4-(CH_2)_n-CHOH-(CH_2)_n-O$-polysaccharide wherein n and m are each 0–10, and
  iv) guanidine and aminoguanidine derivatives selected from the group consisting of
    a) $H_2N-C(=NH)$-polysaccharide
    b) $H_2N-C(=NH)-(CH_2)_n$-polysaccharide
    c) $H_2N-C(=NH)-O-(CH_2)_n$-polysaccharide
    d) $H_2N-C(=NH)-NH$-polysaccharide
    e) $H_2N-C(=NH)-NH-(CH_2)_n$-polysaccharide
    f) $H_2N-C(=NH)-NH-(CH_2)_n-O$-polysaccharide
    g) $H_2N-C(=NH)-N=CH-(CH_2)_n$-polysaccharide
    h) $H_2N-C(=NH)-N=CH-(CH_2)_n-O$-polysaccharide
    i) $H_2N-NHC(=NH)-NH$-polysaccharide
    j) $H_2N-NHC(=NH)-NH-(CH_2)_n$-polysaccharide
    k) $H_2N-NHC(=NH)-NH-(CH_2)_n-O$-polysaccharide
    l) $H_2N-NHC(=NH)-N=CH-(CH_2)_n$-polysaccharide
    m) $H_2N-NHC(=NH)-N=CH-(CH_2)_n-O$-polysaccharide
    n) $H_2N-C(=NH)-NH-NH$-polysaccharide
    o) $H_2N-C(=NH)-NH-NH-(CH_2)_n$-polysaccharide
    p) $H_2N-C(=NH)-NH-NH-(CH_2)_n-O$-polysaccharide
    q) $H_2N-C(=NH)-NH-N=CH-(CH_2)_n$-polysaccharide
    r) $H_2N-C(=NH)-NH-N=CH-(CH_2)_n-O$-polysaccharide wherein n=1–10 unless otherwise stated;

d. primary amine, aminoguanidine and guanidine derivatives of sucrose polyesters having one or more said derivative groups per molecule wherein said derivative group is on a fatty acyl chain, wherein the fatty acyl chains have from 3 to 26 carbons and wherein each fatty acyl chain has from one to 24 hydroxyl groups;

e. synthetic polysaccharides containing aminosugars bound by β-1,2, β-1,3, β-1,4 and/or β-1,6 linkages;

f. primary amine, aminoalkyl, amino(hydroxyalkyl), aminoguanidine, aminoguanidinylalkyl, aminoalkylguanidinyl, guanidine, aminobenzyl, aminoalkylbenzyl derivatives of polysaccharides consisting of more than one polysaccharide polymer wherein the alkyl groups) have 1–10 carbons; and g. primary amine, aminoalkyl, amino(hydroxyalkyl), aminoguanidine, aminoguanidinylalkyl, aminoalkylguanidinyl, guanidine, aminobenzyl, aminoalkylbenzyl derivatives of non-digestible, non-polysaccharide polymers selected from the group consisting of polystyrene, styrene-divinylbenzene copolymer, polyvinyl alcohol and crosslinked derivatives thereof.

19. The method of claim 2 wherein the co-agent of the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity is selected from the group consisting of a) at least one anti-oxidant and free radical trapping compound selected from the group consisting of α-tocopherol, β-tocopherol, γ-tocopherol, δ-tocopherol, ε-tocopherol, $\zeta_1$-tocopherol, $\zeta_2$-tocopherol and η-tocopherol, and pharmaceutically acceptable ester derivatives thereof, with the proviso that said tocopherol substances are used for adult human consumption in a dosage no less than 50 I.U. daily; β-carotene; vitamin A; butylated hydroxytoluene; butylated hydroxyanisole; propyl gallate; dodecylgallate; tert-butylhydroquinone; citric acid; cysteine; ubiquinols; glutathione; dihydrolipoic acid; N-acetylcysteine; prostaglandin $B_1$ oligomers; 2-aminomethyl-4-tert-butyl-6-iodophenol; 2-aminomethyl-4-tert-butyl-6-propionylphenol; 2,6-di-tert-butyl-4-[2'-thenoyl]-phenol; N,N'-diphenyl-p-phenylenediamine; ethoxyquin; probucol; parthenolide; lycopene; daidzin; genistein; quercetin; morin; curcumin; apigenin; sesamol; chlorogenic acid; fisetin; ellagic acid; quillaia saponin; capsaicin; ginsenoside; silymarin; kaempferol; ginkgetin; bilobetin; isoginkgetin; isorhamnetin; herbimycin; rutin; bromelain; levendustin A; and erbstatin, b) a compound having indirect anti-oxidant properties selected from the group consisting of selenium and seleno-containing amino acids, c) a vitamin selected from the group consisting of vitamin A; retinal; retinoic acid; retinyl acetate; thiamine; thiamine propyl disulfide; riboflavin; riboflavin tetrabutyrate; riboflavine 5'-phosphate ester monosodium salt; pyridoxine; pyridoxal; pyridoxal HCl; pyridoxal 5-phosphate; pyridoxal 5-phosphate calcium salt; pyridoxamine; pyridoxamine dihydrochloride; pyridoxamine phosphate; cyanocobalamin; co-methylcobalamin; vitamin $D_2$; vitamin $D_3$; vitamin $D_4$; biotin; vitamin $K_1$; vitamin $K_1$ oxide; vitamins of the $K_2$ series; vitamin $K_5$; vitamin $K_5$ hydrochloride; vitamin $K_6$; vitamin $K_6$ dihydrochloride; vitamin $K_7$; vitamin $K_7$ hydrochloride; vitamin K-S(II); vitamin $L_1$; vitamin $L_2$; vitamin U; methylmethioninesulfonium bromide; α-carotene; β-carotene; γ-carotene; ω-carotene; ψ-,ψ-carotene; 7,7',8,8',11,12-hexahydro-ψ-,ψ-carotene; carnitine; acetyl-L-carnitine; folic acid; folinic acid; folinic acid calcium salt pentahydrate; niacinamide; nicotinic acid; nicotinic acid sodium salt sesquihydrate; nicotinic acid monoethanolamine salt; pantothenic acid; pantothenic acid sodium salt; and pantothenic acid calcium salt, d) a chemical conjugating substance which facilitates kidney drug elimination selected from the group consisting of glycine and pharmaceutically acceptable derivatives thereof, e) a metabolite at risk of depletion selected from the group consisting of pantothenic acid and pharmaceutically acceptable derivatives thereof, f) a sulfhydryl compound selected from the group consisting of homocysteine, acetylhomocysteine thiolactone, L-methionine or α-lipoic acid, or g) a chemical which acts to facilitate glutathione activity, selected from the group consisting of N-acetylcysteine, L-2-oxothiazolidine-4-carboxylate, timonacic, cysteamine, malotilate, sulfarlem, oltipraz and glutathione.

20. The composition of claim 11 wherein the co-agent of the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity is selected from the group consisting of a) at least one anti-oxidant and free radical trapping compound selected from the group consisting of α-tocopherol, β-tocopherol, γ-tocopherol, δ-tocopherol, ε-tocopherol, $ζ_1$-tocopherol, $ζ_2$-tocopherol and η-tocopherol, and pharmaceutically acceptable ester derivatives thereof, with the proviso that said tocopherol substances are used for adult human consumption in a dosage no less than 50 I.U. daily; β-carotene; vitamin A; butylated hydroxytoluene; butylated hydroxyanisole; propyl gallate; dodecylgallate; tert-butylhydroquinone; citric acid; cysteine; ubiquinols; glutathione; dihydrolipoic acid; N-acetylcysteine; prostaglandin $B_1$ oligomers 2-aminomethyl-4-tert-butyl-6-iodophenol; 2-aminomethyl-4-tert-butyl-6-propionylphenol; 2,6-di-tert-butyl-4-[2'-thenoyl]-phenol; N,N'-diphenyl-p-phenylenediamine; ethoxyquin; probucol; parthenolide; lycopene; daidzin; genistein; quercetin; morin; curcumin; apigenin; sesamol; chlorogenic acid; fisetin; ellagic acid; quillaia saponin; capsaicin; ginsenoside; silymarin; kaempferol; ginkgetin; bilobetin; isoginkgetin; isorhamnetin; herbimycin; rutin; bromelain; levendustin A; and erbstatin, b) a compound having indirect anti-oxidant properties selected from the group consisting of selenium and seleno-containing amino acids, c) a vitamin selected from the group consisting of vitamin A; retinal; retinoic acid; retinyl acetate; thiamine; thiamine propyl disulfide; riboflavin; riboflavin tetrabutyrate; riboflavine 5'-phosphate ester monosodium salt; pyridoxine; pyridoxal; pyridoxal HCl; pyridoxal 5-phosphate; pyridoxal 5-phosphate calcium salt; pyridoxamine; pyridoxamine dihydrochloride; pyridoxamine phosphate; cyanocobalamin; co-methylcobalamin; vitamin $D_2$; vitamin $D_3$; vitamin $D_4$; biotin; vitamin $K_1$; vitamin $K_1$ oxide; vitamins of the $K_2$ series; vitamin $K_5$; vitamin $K_5$ hydrochloride; vitamin $K_6$; vitamin $K_6$ dihydrochloride; vitamin $K_7$; vitamin $K_7$ hydrochloride; vitamin K-S(II); vitamin $L_1$; vitamin $L_2$; vitamin U; methylmethioninesulfonium bromide; α-carotene; β-carotene; γ-carotene; ω-carotene; ψ-,ψ-carotene; 7,7',8,8',11,12-hexahydro-ψ-,ψ-carotene; carnitine; acetyl-L-carnitine; folic acid; folinic acid; folinic acid calcium salt pentahydrate; niacinamide; nicotinic acid; nicotinic acid sodium salt sesquihydrate; nicotinic acid monoethanolamine salt; pantothenic acid; pantothenic acid sodium salt; and pantothenic acid calcium salt, d) a chemical conjugating substance which facilitates kidney drug elimination selected from the group consisting of glycine and pharmaceutically acceptable derivatives thereof, e) a metabolite at risk of depletion selected from the group consisting of pantothenic acid and pharmaceutically acceptable derivatives thereof, f) a sulfhydryl compound selected from the group consisting of homocysteine, acetylhomocysteine thiolactone, L-methionine or α-lipoic acid, or g) a chemical which acts to facilitate glutathione activity, selected from the group consisting of N-acetylcysteine, L-2-oxothiazolidine-4-carboxylate, timonacic, cysteamine, malotilate, sulfarlem, oltipraz and glutathione.

21. The composition of claim 11 wherein the co-agent that is a non-digestible polyamine is selected from a compound of claim 18.

22. A composition for treating a mammalian subject for symptoms of a chronic inflammatory disorder, said composition consisting essentially of (a) a therapeutically effective amount of a primary agent consisting of a water soluble primary amine compound having a molecular weight in the range of 100 to about 1,400 of the formula $$R_1 \diagup\!\!\!\diagup\!\!\!\diagdown\!\!\!\diagdown\!\!\!-(C)_m-COOH$$
with $R'$ above and $R''$ below the (C), and $R_2$ on the ring wherein the 6-membered ring is phenyl, cyclohexadiene, cyclohexene or cyclohexane; and wherein $R_1$ is —$NH_2$; aminoalkyl- having 1–10 carbons; —NHC(=NH)$NH_2$; —$(CH_2)_n$NHC(=NH)$NH_2$ wherein n is 1–10; —C(=NH)$NH_2$; —$(CH_2)_n$—CH=NC(=NH)$NH_2$ wherein n is 1–10; —NHC(=NH)NHNH$_2$; —$(CH_2)_n$NHC(=NH)NHNH$_2$ wherein n is 1–10; —$(CH_2)_n$—CH=NC(=NH)NHNH$_2$ wherein n is 1–10; —NHNHC(=NH)$NH_2$; —$(CH_2)_n$—NHNHC(=NH)$NH_2$ wherein n is 1–10; or —$(CH_2)_n$—CH=N—NHC(=NH)$NH_2$ wherein n is 1–10;

R$_2$ is H; —OH; —O—CH$_3$; —O—R wherein R is alkyl of 2–10 carbons; aminoalkyl wherein the alkyl group is 1–10 carbons; —SO$_3$H; —CH$_3$; and —(CH$_2$)$_n$CH$_3$ wherein n is 1–10;

R' and R" are —H, OH or CH$_3$; and m is 0 or 1;

and the pharmaceutically acceptable salts, esters, and amide derivatives thereof; and (b) a therapeutically effective amount of at least one co-agent selected from the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity; and (c) a therapeutically effective amount of an additional co-agent that is a non-digestible polyamine; and (d) a pharmaceutically acceptable carrier;

wherein the amount of the primary agent on a molar basis is always greater than that of a co-agent.

23. A composition according to claim 22 wherein the pharmaceutically acceptable carrier is an aqueous solution or suspension for oral use, a comestible product for oral use, or a combination thereof.

24. A composition according to claim 23 wherein the comestible product for oral use is a capsule, a sustained-release capsule, a tablet, a sustained-release tablet or a foodstuff.

25. The composition of claim 22 wherein the co-agent of the group consisting of an anti-oxidant and free radical trapping compound with the proviso that dimethyl sulfoxide is exempted from this group, a compound having indirect anti-oxidant activity, a vitamin, a compound having conjugating activity which facilitates kidney drug elimination, a metabolite at risk of depletion, a sulfhydryl compound and a compound which facilitates glutathione activity is selected from the group consisting of a) at least one anti-oxidant and free radical trapping compound selected from the group consisting of α-tocopherol, β-tocopherol, γ-tocopherol, δ-tocopherol, ε-tocopherol, ζ$_1$-tocopherol, ζ$_2$-tocopherol and η-tocopherol, and pharmaceutically acceptable ester derivatives thereof, with the proviso that said tocopherol substances are used for adult human consumption in a dosage no less than 50 I.U. daily; β-carotene; vitamin A; butylated hydroxytoluene; butylated hydroxyanisole; propyl gallate; dodecyl-gallate; tert-butylhydroquinone; citric acid; cysteine; ubiquinols; glutathione; dihydrolipoic acid; N-acetylcysteine; prostaglandin B$_1$ oligomers; 2-aminomethyl-4-tert-butyl-6-iodophenol; 2-aminomethyl-4-tert-butyl-6-propionylphenol; 2,6-di-tert-butyl-4-[2'-thenoyl]-phenol; N,N'-diphenyl-p-phenylenediamine; ethoxyquin; probucol; parthenolide; lycopene; daidzin; genistein; quercetin; morin; curcumin; apigenin; sesamol; chlorogenic acid; fisetin; ellagic acid; quillaia saponin; capsaicin; ginsenoside; silymarin; kaempferol; ginkgetin; bilobetin; isoginkgetin; isorhamnetin; herbimycin; rutin; bromelain; levendustin A; and erbstatin, b) a compound having indirect anti-oxidant properties selected from the group consisting of selenium and seleno-containing amino acids, c) a vitamin selected from the group consisting of vitamin A; retinal; retinoic acid; retinyl acetate; thiamine; thiamine propyl disulfide; riboflavin; riboflavin tetrabutyrate; riboflavine 5'-phosphate ester monosodium salt; pyridoxine; pyridoxal; pyridoxal HCl; pyridoxal 5-phosphate; pyridoxal 5-phosphate calcium salt; pyridoxamine; pyridoxamine dihydrochloride; pyridoxamine phosphate; cyanocobalamin; co-methylcobalamin; vitamin D$_2$; vitamin D$_3$; vitamin D$_4$; biotin; vitamin K$_1$; vitamin K$_1$ oxide; vitamins of the K$_2$ series; vitamin K$_5$; vitamin K$_5$ hydrochloride; vitamin K$_6$; vitamin K$_6$ dihydrochloride; vitamin K$_7$; vitamin K$_7$hydrochloride; vitamin K-S(II); vitamin L$_1$; vitamin L$_2$; vitamin U; methylmethioninesulfonium bromide; α-carotene; β-carotene; γ-carotene; ω-carotene; ψ-,ψ-carotene; 7,7',8,8',11,12-hexahydro-ψ-,ψ-carotene; carnitine; acetyl-L-carnitine; folic acid; folinic acid; folinic acid calcium salt pentahydrate; niacinamide; nicotinic acid; nicotinic acid sodium salt sesquihydrate; nicotinic acid monoethanolamine salt; pantothenic acid; pantothenic acid sodium salt; and pantothenic acid calcium salt, d) a chemical conjugating substance which facilitates kidney drug elimination selected from the group consisting of glycine and pharmaceutically acceptable derivatives thereof, e) a metabolite at risk of depletion selected from the group consisting of pantothenic acid and pharmaceutically acceptable derivatives thereof, f) a sulfhydryl compound selected from the group consisting of homocysteine, acetylhomocysteine thiolactone, L-methionine or α-lipoic acid, or g) a chemical which acts to facilitate glutathione activity, selected from the group consisting of N-acetylcysteine, L-2-oxothiazolidine-4-carboxylate, timonacic, cysteamine, malotilate, sulfarlem, oltipraz and glutathione.

26. The composition of claim 22 wherein the co-agent that is a non-digestible polyamine is selected from a compound of claim 18.

* * * * *